US007795504B2

(12) United States Patent
Van Eenennaam et al.

(10) Patent No.: US 7,795,504 B2
(45) Date of Patent: Sep. 14, 2010

(54) COORDINATED DECREASE AND INCREASE OF GENE EXPRESSION OF MORE THAN ONE GENE USING TRANSGENIC CONSTRUCTS

(75) Inventors: Alison Van Eenennaam, Davis, CA (US); Christine K. Shewmaker, Woodland, CA (US)

(73) Assignee: Monsanto Technology LLC, St. Louis, MO (US)

( * ) Notice: Subject to any disclaimer, the term of this patent is extended or adjusted under 35 U.S.C. 154(b) by 619 days.

(21) Appl. No.: 11/633,469

(22) Filed: Dec. 5, 2006

(65) Prior Publication Data

US 2007/0074305 A1   Mar. 29, 2007

Related U.S. Application Data

(63) Continuation of application No. 10/668,240, filed on Sep. 24, 2003, now Pat. No. 7,166,771.

(51) Int. Cl.
*A01H 5/00* (2006.01)
*C12N 15/82* (2006.01)
*C07H 21/04* (2006.01)
(52) U.S. Cl. .................. 800/298; 800/281; 536/23.1
(58) Field of Classification Search .................. None
See application file for complete search history.

(56) References Cited

U.S. PATENT DOCUMENTS

| 4,557,734 | A | 12/1985 | Schwab et al. |
| 5,454,842 | A | 10/1995 | Poirier et al. |
| 5,475,099 | A | 12/1995 | Knauf et al. |
| 5,500,361 | A | 3/1996 | Kinney |
| 5,627,061 | A | 5/1997 | Barry et al. |
| 5,633,435 | A | 5/1997 | Barry et al. |
| 5,714,670 | A | 2/1998 | Fehr et al. |
| 5,723,595 | A | 3/1998 | Thompson et al. |
| 5,723,761 | A | 3/1998 | Voelker et al. |
| 5,850,026 | A | 12/1998 | Debonte et al. |
| 5,888,947 | A | 3/1999 | Lambert et al. |
| 5,891,203 | A | 4/1999 | Ball et al. |
| 5,955,329 | A | 9/1999 | Yuan et al. |
| 5,955,650 | A | 9/1999 | Hitz |
| 6,013,114 | A | 1/2000 | Hille et al. |
| 6,150,512 | A | 11/2000 | Yuan |
| 6,331,664 | B1 | 12/2001 | Rubin-Wilson et al. |
| 6,369,296 | B1 | 4/2002 | Ratcliff et al. |
| 6,372,965 | B1 | 4/2002 | Lightner et al. |
| 6,380,462 | B1 | 4/2002 | Kridl |
| 6,506,559 | B1 | 1/2003 | Fire et al. |
| 6,573,099 | B2 | 6/2003 | Graham |
| 7,166,771 | B2 * | 1/2007 | Eenennaam et al. ......... 800/298 |
| 2002/0034814 | A1 | 3/2002 | Atabekov et al. |
| 2003/0049835 | A1 | 3/2003 | Helliwell et al. |
| 2003/0135882 | A1 | 7/2003 | Metzlaff et al. |
| 2003/0172399 | A1 | 9/2003 | Fillatti |
| 2004/0107460 | A1 | 6/2004 | Fillatti et al. |
| 2004/0126845 | A1 | 7/2004 | Eenennaam et al. |
| 2005/0034190 | A9 | 2/2005 | Fillatti et al. |

FOREIGN PATENT DOCUMENTS

| EP | 0 959 133 A1 | 11/1999 |
| WO | WO 94/10189 A1 | 5/1994 |
| WO | WO 94/11516 A1 | 5/1994 |
| WO | WO 96/06936 | 3/1996 |
| WO | WO 93/11245 A1 | 6/1996 |
| WO | WO 98/05770 A2 | 2/1998 |
| WO | WO 98/30083 A1 | 7/1998 |
| WO | WO 98/46776 A2 | 10/1998 |
| WO | WO 98/53083 A1 | 11/1998 |
| WO | WO 99/15682 A2 | 4/1999 |
| WO | WO 99/32619 A1 | 7/1999 |
| WO | WO 99/49029 A1 | 9/1999 |
| WO | WO 99/53050 A1 | 10/1999 |
| WO | WO 99/61631 A1 | 12/1999 |
| WO | WO 99/64579 A2 | 12/1999 |
| WO | WO 00/07432 A1 | 2/2000 |
| WO | WO 00/18880 | 4/2000 |
| WO | WO 00/44895 A1 | 8/2000 |
| WO | WO 00/44914 A1 | 8/2000 |

(Continued)

OTHER PUBLICATIONS

Bosher et al., "RNA Interference Can Target Pre-mRNA: Consequences for Gene Expression in a *Caenorhabditis elegans* Operon", *Genetics*, 153:1245-1256 (1999).

Bouchon et al., "Oil Distribution in Fried Potatoes Monitored by Infrared Microspectroscopy", *Journal of Food Science*, 66(7):918-923 (2001), Provided in U.S. Appl. No. 10/668,240.

Buhr et al., "Ribozyme Termination of RNA Transcripts Down-Regulate Seed Fatty Acid Genes in Transgenic Soybean", *The Plant Journal*, 30(2):155-163 (2002), Provided in U.S. Appl. No. 10/668,240.

Cartea et al., "Comparison of Sense and Antisense Methodologies for Modifying the Fatty Acid Composition of *Arabidopsis thaliana* Oilseed", *Plant Science*, 136, 181-194 (1998), Provided in U.S. Appl. No. 10/668,240.

(Continued)

*Primary Examiner*—Elizabeth F McElwain
(74) *Attorney, Agent, or Firm*—Thomas E. Kelley; Arnold & Porter LLP

(57) ABSTRACT

The present invention is directed to nucleic acid molecules and nucleic acid constructs, and other agents associated with simultaneous up- and down-regulation of expression of RNAs. Specifically it includes methods of simultaneously enhancing the expression of a first RNA at the same time as suppressing the expression of a second RNA. The present invention also specifically provides constructs capable of simultaneously enhancing the expression of a first RNA while at the same time suppressing the expression of a second RNA, methods for utilizing such agents and plants containing such agents. The present invention also provides other constructs including polycistronic constructs.

7 Claims, 5 Drawing Sheets

FOREIGN PATENT DOCUMENTS

| WO | WO 00/68374 A1 | 11/2000 |
|---|---|---|
| WO | WO 01/11061 A2 | 2/2001 |
| WO | WO 01/14538 A2 | 3/2001 |
| WO | WO 01/14538 A3 | 3/2001 |
| WO | WO 01/34822 A2 | 5/2001 |
| WO | WO 01/35726 A1 | 5/2001 |
| WO | WO 01/36598 A1 | 5/2001 |
| WO | WO 01/70949 A1 | 9/2001 |
| WO | WO 01/79499 A1 | 10/2001 |
| WO | WO 02/04581 A1 | 1/2002 |
| WO | WO 02/15675 A1 | 2/2002 |
| WO | WO 02/059336 A2 | 8/2002 |
| WO | WO 02/081711 A1 | 10/2002 |
| WO | WO 02/088301 A2 | 11/2002 |
| WO | WO 03/080802 A2 | 10/2003 |

OTHER PUBLICATIONS

Chuang et al., "Specific and Heritable Genetic Interference by Double-Stranded RNA in *Arabidopsis thaliana*", *PNAS*, 97(9):4985-4990 (2000).

Clark-Walker et al., "Location of Transcriptional Control Signals and Transfer RNA Sequences in *Torulopsis glabrata* Mitochondrial DNA", *EMBO (European Molecular Biology Organization) Journal*, 4(2):465-473 (1985), Provided in U.S. Appl. No. 10/668,240.

Cogoni, C. et al., "Post-Transcriptional Gene Silencing Across Kingdoms", *Curr. Opin. Gen. & Devel.*, 10(6):638-643 (2000), Provided in U.S. Appl. No. 10/668,240.

Colliver et al., "Differential modification of flavonoid and isoflavonoid biosynthesis with an antisense chalcone synthase construct in transgenic *Lotus corniculatus*", *Plant Mol. Biol.*, 35:509-522 (1997).

Crossway, A. et al., "Integration of Foreign DNA Following Microinjection of Tobacco Mesophyll Protoplasts", *Mol. Gen. Genet.*, 202(2):179-185 (1986), Provided in U.S. Appl. No. 10/668,240.

DeLuca, "Molecular characterization of secondary metabolic pathways", *AgBiotech News and Information*, 5(6):225N-229N (1993).

Dörmann, P. et al., "Accumulation of Palmitate in *Arabidopsis* Mediated by the Acyl-Acyl Carrier Protein Thioesterase FATB1", *Plant Physiology*, 123:637-643 (2000), Provided in U.S. Appl. No. 10/668,240.

Database EM_GSS 'Online! EMBL Heidelberg, Germany; AC AL071390, May 29, 1999, GENOSCOPE: "*Drosophila melanogaster* genome surface sequence TET3 end of BAC: BACR32MO5", XP002163063, abstract, Provided in U.S. Appl. No. 10/668,240.

Database EMPLN 'Online! EMBL Heidelberg, Germany; AC/ID AC004705, May 21, 1998, Lin X et al.: "Sequence and analysis of chromosome 2 of the plant *Arabidopsis thaliana*" XP002163064, abstract, Provided in U.S. Appl. No. 10/668,240.

Database EM_GSS 'Online! EMBL Heidelberg, Germany; AC AL105179, Jul. 26, 1999, GENOSCOPE: "*Drosophila melanogaster* genome survey sequence T7 end of BAC: BACN13A12" XP002163065, abstract, Provided in U.S. Appl. No. 10/668,240.

Database EM-NEW 'Online! EMBL Heidelberg, Germany; AC/ID AB022220, Jan. 15, 1999, Sato S. et al.: "*Arabidopsis thaliana* genomic DNA, chromosome 3, P1 clone: MLN21" XP002163066, abstract, Provided in U.S. Appl. No. 10/668,240.

Database EM_GSS 'Online! EMBL Heidelberg, Germany; AC AL069706, May 29, 1999, GENOSCOPE: "*Drosophila melanogaster* genome survey sequence T7 end of BAC: BACR29B23" XP002163067, abstract, Provided in U.S. Appl. No. 10/668,240.

Database EM_GSS 'Online! EMBL Heidelberg, Germany; AC AL063932, May 29, 1999, GENOSCOPE; "*Drosophila melanogaster* genome survey sequence TET3 end of BAC: BACR8010" XP002163068, abstract, Provided in U.S. Appl. No. 10/668,240.

Database EM_GSS 'Online! EMBL Heidelberg, Germany; AC AL108811, Jul. 26, 1999, GENOSCOPE: "*Drosophila melanogaster* genome survey sequence SP6 end of BAC BACN37D10" XP002163069, abstract, Provided in U.S. Appl. No. 10/668,240.

Database EM_NEW 'Online! EMBL Heidelberg, Germany; AC/ID AB026636, May 7, 1999, Sato S. et al.: "*Arabidopsis thaliana* genomic DNA, chromosome 3, TAC clone: K14A17", XP002163070, abstract, Provided in U.S. Appl. No. 10/668,240.

Database EMEST_PLN 'Online! EMBL Heidelberg, Germany; AC/ID AW297948, Feb. 8, 2000, Shoemaker R. et al.: "Public soybean EST project", XP002163071, abstract, Provided in U.S. Appl. No. 10/668,240.

Database EMPLN 'Online! EMBL Heidelberg, Germany; AC AL161581, Mar. 15, 2000, Weichselgartner M. et al.: "*Arabidopsis thaliana* chromosome 4, contig fragment No. 77", XP002163072, abstract, Provided in U.S. Appl. No. 10/668,240.

Duffield, J. et al., "U.S. Biodiesel Development: New Markets for Conventional and Genetically Modified Agricultural Products", *Economic Research Service USDA*, pp. 1-31 (1998), Provided in U.S. Appl. No. 10/668,240.

Dunn, R. et al., "Recent Advances in the Development of Alternative Diesel Fuel from Vegetable Oils and Animal Fats", *Recent Res. Devel. in Oil Chem.*, 1:31-56 (1997), Provided in U.S. Appl. No. 10/668,240.

Erhan, S. et al., "Lubricant Basestocks from Vegetable Oils", *Industrial Crops and Products*, 11:277-282 (2000), Provided in U.S. Appl. No. 10/668,240.

Fire, A. et al., "Potent and Specific Genetic Interference by Double-Stranded RNA in *Caenorhabditis elegans*", *Nature*, 391:806-811 (1998), Provided in U.S. Appl. No. 10/668,240.

Halpin, C. et al., "Enabling Technologies for Manipulating Multiple Genes on Complex Pathways", *Plant Molecular Biology*, 47:295-310 (2001), Provided in U.S. Appl. No. 10/668,240.

Hamada, T. et al., "Modification of Fatty Acid Composition by Over- and Antisense-Expression of a Microsomal ω-3 Fatty Acid Desaturase Gene in Transgenic Tobacco", *Transgenic Research*, 5(2), 115-121 (1996), Provided in U.S. Appl. No. 10/668,240.

Hamilton et al., "A Transgene with Repeated DNA Causes High Frequency, Post-Transcriptional Suppression of ACC-Oxidase Gene Expression in Tomato", *The Plant Journal*, 15(6):737-746 (1998).

International Search Report mailed Nov. 13, 2003 in PCT/US03/08610, Provided in U.S. Appl. No. 10/668,240.

International Search Report mailed Jul. 12, 2005, issued in PCT/US04/31605, Provided in U.S. Appl. No. 10/668,240.

International Search Report mailed Apr. 9, 2004, issued in PCT/US03/19445, Provided in U.S. Appl. No. 10/668,240.

International Search Report of International Application No. PCT/US2003/019437 dated Jun. 21, 2004.

International Search Report mailed Apr. 26, 2001, issued in PCT/US00/22613, Provided in U.S. Appl. No. 10/668,240.

Jaworski et al., "Industrial oils from transgenic plants", *Current Opinion in Plant Biology*, 6:178-184 (2003).

Lee et al., "Antisense Expression of the CK2 α-Subunit Gene in *Arabidopsis*. Effects on Light-Regulated Gene Expression and Plant Growth", *Plant Physiology*, 119:989-1000 (1999), Provided in U.S. Appl. No. 10/668,240.

Levin et al., "Methods of Double-Stranded RNA-Mediated Gene Inactivation in *Arabidopsis* and Their Use to Define an Essential Gene in Methionine Biosynthesis", *Plant Mol. Biol.*, 44(6):759-775 (2000).

Lewin, B., "How Did Interrupted Genes Evolve?", *Genes*, 2$^{nd}$ Edition, pp. 333-337 , 1985, Provided in U.S. Appl. No. 10/668,240.

Matzke, M.A. et al., "RNA-Based Silencing Strategies in Plants", *Curr. Opin. Gen. & Devel.*, 11(2):221-227 (2001), Provided in U.S. Appl. No. 10/668,240.

Mensink, R. et al., "Effect of Dietary Fatty Acids on Serum Lipids and Lipoproteins: A Meta-Analysis of 27 Trials", *Arteriosclerosis and Thrombosis*, 12(8):911-919 (1992), Provided in U.S. Appl. No. 10/668,240.

Montgomery, M.K. et al., "RNA as a Target of Double-Stranded RNA-Mediated Genetic Interference in *Caenorhabditis elegans*", *Proc. Natl. Acad. Sci. USA*, 95(96):15502-15507 (1998), Provided in U.S. Appl. No. 10/668,240.

Napoli, C. et al., "Introduction of a Chimeric Chalcone Synthase Gene into Petunia Results in Reversible Co-Suppression of Homologous Genes in trans", *The Plant Cell*, 2:279-289 (1990), Provided in U.S. Appl. No. 10/668,240.

Neff, W.E. et al., "Odor Significance of Undersirable Degradation Compounds in Heated Triolein and Trilinolein", *JAOCS*, 77(12):1303-1313 (2000), Provided in U.S. Appl. No. 10/668,240.

Okuley, J., et al., "*Arabidopsis* FAD2 Gene Encodes the Enzyme that is Essential for Polyunsaturated Lipid Synthesis", *The Plant Cell*, 6:147-158 (1994), Provided in U.S. Appl. No. 10/668,240.

Padgette et al., *Crop Sci.*, "Development, Identification, and Characterization of a Glyphosate-Tolerant Soybean Line", 35:1451-1461 (1995).

Peele et al., "Silencing of a meristematic gene using geminivirus-derived vectors", *The Plant Journal*, 27(4):357-366 (2001).

Qing, L., Thesis, "The Isolation and Characterisation of Fatty Acid Desaturase Genes in Cotton", University of Sydney, Australia, pp. ii-iv, 24-26, 121-123, 142, 167-168, 172-174, 179-181 (1998), Provided in U.S. Appl. No. 10/668,240.

Sharp, P.A., "RNAi and Double-Strand RNA", *Genes & Development*, 13:139-141 (1999), Provided in U.S. Appl. No. 10/668,240.

Sharp, P.A., "RNA Interference-2001", *Genes & Development*, 15:485-490 (2001), Provided in U.S. Appl. No. 10/668,240.

Singh et al., "Metabolic engineering of new fatty acids in plants", *Current Opinion in Plant Biology*, 8:197-203 (2005).

Smith et al., "Total silencing by intron-spliced hairpin RNAs", *Nature*, 407:319-320 (2000).

Stam et al., "Post-transcriptional silencing of chalcone synthase in *Petunia* by inverted transgene repeats", *The Plant Journal* 12(1):63-82 (1997).

Stoutjeskijk et al., "hpRNA-Mediated Targeting of the *Arabidopsis* FAD 2 Gene Gives Highly Efficient and Stable Silencing", *Plant Physiology*, 129:1723-1731 (2002).

Supplemental European Search Report in European Application No. 03711656.3 completed Jun. 29, 2005, Provided in U.S. Appl. No. 10/668,240.

Supplementary European Search Report European Application No. 04 78 5109 (Nov. 7, 2006).

Supplementary Partial European Search Report in Application No. 03 76 1158 dated Jan. 8, 2007.

Timmons, J.S. et al., "Relationships Among Dietary Roasted Soybeans, Milk Components, and Spontaneous Oxidized Flavor of Milk", *Journal of Diary Science*, 84(11):2440-2449 (2001), Provided in U.S. Appl. No. 10/668,240.

Toborek, M. et al., "Unsaturated Fatty Acids Selectively Induce an Inflammatory Environment in Human Endothelial Cells", *American Journal of Clinical Nutrition*, 75:119-125 (2002), Provided in U.S. Appl. No. 10/668,240.

van der Krol, A. R. et al., "Flavonoid Genes in Petunia: Addition of a Limited Number of Gene Copies May Lead to a Suppression of Gene Expression", *The Plant Cell*, 2:291-299 (1990), Provided in U.S. Appl. No. 10/668,240.

Warner, K. et al., "Effect of Oleic and Linoleic Acids on the Production of Deep-Fried Odor in Heated Triolein and Trilinolein", *Journal of Agricultural Food Chemical*, 49:899-905 (2001), Provided in U.S. Appl. No. 10/668,240.

Waterhouse, P.M. et al., "Virus Resistance and Gene Silencing in Plants Can be Induced by Simultaneous Expression of Sense and Antisense RNA", *Proc. Natl. Acad. Sci. USA*, 95:13959-13964 (1998), Provided in U.S. Appl. No. 10/668,240.

Wesley, S.V. et al., "Construct Design for Efficient, Effective and High-Throughput Gene Silencing in Plants", *The Plant Journal*, 27(6):581-590 (2001), Provided in U.S. Appl. No. 10/668,240.

* cited by examiner

Total Tocopherol in T3 Arabidopsis Seed

% Alpha Tocopherol in T3 Arabidopsis Seed

```
                        SEQUENCE LISTING

<160> NUMBER OF SEQ ID NOS: 6

<210> SEQ ID NO 1
<211> LENGTH: 1038
<212> TYPE: DNA
<213> ORGANISM: Gossypium hirsutum

<400> SEQUENCE: 1
atggctgccg cgttacaatt acaaacacac ccttgcttcc atggcacgtg ccaactctca      60
cctccgccac gaccttccgt ttccttccct tcttcctccc gctcgtttcc atctagcaga     120
cgttccctgt ccgcgcatgt gaaggcggcg gcgtcgtctt tgtccaccac caccttgcag     180
gaagggatag cggagtttta cgatgagtcg tcggggattt gggaagacat atgggggtgac    240 catatgcacc atggatatta cgagccgggt tccgatattt cgggttcaga tcatcgtgcc     300
gctcagattc gaatggtcga agaatcgctc cgttttgctg aatatcaga ggacccagca      360 aacaggccca agagaatagt tgatgttggg tgtgggatag gaggcagttc taggtatcta     420
gcaaggaaat atgggggcaaa atgccaaggc attactttga gccctgttca agctggaaga    480
gccaatgctc ttgctaatgc tcaaggacta gcagaacagg tttgttttga agttgcagat     540
gccttgaacc aaccattccc tgatgaccaa tttgatcttg tttggtctat ggaaagcgga     600
gaacacatgc ctgacaaacc caagtttgtt aaagagctgt gcgagtggc agctccagga     660 ggcacaataa tagtagtgac atggtgccat agggatcttg gtccatctga agagtctttg     720
cagccatggg agcaaaagct tttaaacaga atatgtgatg cttactattt accagagtgg     780
tgttctactt ctgattatgt caaattattt cagtccctat ctctccagga tataaaggca     840
ggagactgga ctgagaatgt agcacccttt tggccagcag tgatacgttc agcattgaca     900
tggaagggct tcacatcgct gctacgaagt ggattaaaaa caataaaagg tgcactggtg    960
atgccattga tgatcgaagg tttccagaaa gggggtgataa agtttgccat cattgcttgc  1020
cggaagccag ctgagtag                                                 1038
```

<210> SEQ ID NO 2
<211> LENGTH: 62
<212> TYPE: DNA
<213> ORGANISM: Artificial sequence
<220> FEATURE:
<223> OTHER INFORMATION: Synthetic Primer

<400> SEQUENCE: 2
ggggacaagt tgtacaaaa aagcaggctg cggccgcaca atggctgccg cgttacaatt    60
ac                                                                 62

<210> SEQ ID NO 3
<211> LENGTH: 57
<212> TYPE: DNA
<213> ORGANISM: Artificial Sequence
<220> FEATURE:
<223> OTHER INFORMATION: Synthetic Primer

<400> SEQUENCE: 3
ggggaccact ttgtacaaga aagctgggtc ctgcaggcta ctcagctggc ttccggc      57

<210> SEQ ID NO 4
<211> LENGTH: 1405
<212> TYPE: DNA
<213> ORGANISM: Artificial sequence
<220> FEATURE:
<223> OTHER INFORMATION: Synthetic Primer

<400> SEQUENCE: 4
cgcccttcgg ccgcgcatga tggtgaagaa attgtcgacc tttctcttgt ctgtttgtct    60
tttgttaaag aagctatgct tcgttctaat aatcttattg tccatttttgt tgtgttatga  120 catttttggct gctcccatgg caggtccgtc gcttctcttc catttcttct cattttcgat  180
tttgattctt atttctttcc agtagctcct gctctgtgaa tttctccgct cacgatagat   240
ctgcttatac tccttacatt caaccttaga tctggtctcg attctctgtt tctctgtttt   300
tttcttttgg tcgagaatct gatgtttgtt tatgttctgt caccattaat aataatgaac   360
tctctcattc atacaatgat tagttttctct cgtctacaaa acgatatgtt gcattttcac   420
ttttcttctt tttttctaag atgatttgct ttgaccaatt tgtttagatc tttatttat    480 tttatttttct ggtgggttgg tggaaattga aaaaaaaaa aaacagcata aattgttatt   540
tgttaatgta ttcatttttt ggctatttgt tctgggtaaa aatctgcttc tactattgaa   600
tctttcctgg attttttact cctattgggt ttttatagta aaaatacata ataaaaggaa   660
aacaaaagtt ttatagattc tcttaaaccc cttacgataa aagttggaat caaaataatt   720
caggatcaga tgctctttga ttgattcaga tgcgattaca gttgcatggc aaattttcta   780
gatccgtcgt cacattttat tttctgttta aatatctaaa tctgatatat gatgtcgaca   840
aattctggtg gcttatacat cacttcaact gttttcttttt ggctttgttt gtcaacttgg   900
ttttcaatac gatttgtgat ttcgatcgct gaattttttaa tacaagcaaa ctgatgttaa   960
ccacaagcaa gagatgtgac ctgccttatt aacatcgtat tacttactac tagtcgtatt  1020
ctcaacgcaa tcgttttttgt atttctcaca ttatgccgct tctctactct ttattccttt   1080
tggtccacgc atttttctatt tgtggcaatc cctttcacaa cctgatttcc cacttttggat  1140 catttgtctg aagactctct tgaatcgtta ccacttgttt cttgtgcatg ctctgttttt   1200
tagaattaat gataaaacta ttccatagtc ttgagttttc agcttgttga ttcttttgct   1260
tttggttttc tgcagggtac cgagcagcca aaatgtcaaa acacaacaaa atggacaata   1320

-continued

| | |
|---|---|
| agattattaa aacgaagcat agcttcttta acaaaagaca aacagacaag agaaaggtcg | 1380 |
| acaatttctt caccatcatg ccccg | 1405 |

<210> SEQ ID NO 5
<211> LENGTH: 8179
<212> TYPE: DNA
<213> ORGANISM: Artificial Sequence
<220> FEATURE:
<223> OTHER INFORMATION: Vector

<400> SEQUENCE: 5

| | |
|---|---|
| cgaagctcgg tcccgtgggt gttctgtcgt ctcgttgtac aacgaaatcc attcccattc | 60 |
| cgcgctcaag atggcttccc ctcggcagtt catcagggct aaatcaatct agccgacttg | 120 |
| tccggtgaaa tgggctgcac tccaacagaa acaatcaaac aaacatacac agcgacttat | 180 |
| tcacacgagc tcaaattaca acggtatata tcctgccagt cagcatcatc acaccaaaag | 240 |
| ttaggcccga atagtttgaa attagaaagc tcgcaattga ggtctgcgcc caatacgcaa | 300 |
| accgcctctc cccgcgcgtt ggccgattca ttaatgcagc tggcacgaca ggtttcccga | 360 |
| ctggaaagcg ggcagtgagc gcaacgcaat taatgtgagt tagctcactc attaggcacc | 420 |
| ccaggcttta cactttatgc ttccggctcg tatgttgtgt ggaattgtga gcggataaca | 480 |
| atttcacaca ggaaacagct atgaccatga ttacgaattg taccgaatta tcactacaat | 540 |
| gtcggagaga caaggctgcg ccagcatata caaaagggaa atgaagatgg ccttttgatt | 600 |
| agctgtgtag catcagcagc taatctctgg gctctcatca tggatgctgg aactggattc | 660 |
| acttctcaag tttatgagtt gtcaccggtc ttcctacaca aggtaataat cagttgaagc | 720 |
| aattaagaat caatttgatt tgtagtaaac taagaagaac ttaccttatg ttttccccgc | 780 |
| aggactggat tatggaacaa tgggaaaaga actactatat aagctccata gctggttcag | 840 |
| ataacgggag ctctttagtt gttatgtcaa aaggttagtg tttagtgaat aataaactta | 900 |
| taccacaaag tcttcattga cttatttata tacttgttgt gaattgctag gaactactta | 960 |
| ttctcagcag tcatacaaag tgagtgactc atttccgttc aagtggataa ataagaaatg | 1020 |
| gaaagaagat tttcatgtaa cctccatgac aactgctggt aatcgttggg gtgtggtaat | 1080 |
| gtcgaggaac tctggcttct ctgatcaggt aggttttgt ctcttattgt ctggtgtttt | 1140 |
| tattttcccc tgatagtcta atatgataaa ctctgcgttg tgaaaggtgg tggagcttga | 1200 |
| cttttttgtac ccaagcgatg ggatacatag gaggtgggag aatgggtata gaataacatc | 1260 |
| aatggcagca actgcggatc aagcagcttt catattaagc ataccaaagc gtaagatggt | 1320 |
| ggatgaaact caagagactc tccgcaccac cgccttccca agtactcatg tcaaggttgg | 1380 |
| tttctttagc tttgaacaca gatttggatc tttttgtttt gtttccatat acttaggacc | 1440 |
| tgagagcttt tggttgattt ttttttcagg acaaatgggc gaagaatctg tacattgcat | 1500 |
| caatatgcta tggcaggaca gtgtgctgat acacacttaa gcatcatgtg gaaagccaaa | 1560 |
| gacaattgga gcgagactca gggtcgtcat aataccaatc aaagacgtaa aaccagacgc | 1620 |
| aacctctttg gttgaatgta atgaaaggga tgtgtcttgg tatgtatgta cgaataacaa | 1680 |
| aagagaagat ggaattagta gtagaaatat tgggagcttt tttaagcccct tcaagtgtgc | 1740 |
| tttttatctt attgatatca tccatttgcg ttgtttaatg cgtctctaga tatgttccta | 1800 |
| tatctttctc agtgtctgat aagtgaaatg tgagaaaacc ataccaaacc aaaatattca | 1860 |
| aatcttattt ttaataatgt tgaatcactc ggagttgcca ccttctgtgc caattgtgct | 1920 |
| gaatctatca cactagaaaa aaacatttct tcaaggtaat gacttgtgga ctatgttctg | 1980 |

```
aattctcatt aagttttttat tttctgaagt ttaagttttt accttctgtt ttgaaatata   2040
tcgttcataa gatgtcacgc caggacatga gctacacatc gcacatagca tgcagatcag   2100
gacgatttgt cactcacttc aaacacctaa gagcttctct ctcacagcgc acacacatat   2160
gcatgcaata tttacacgtg atcgccatgc aaatctccat tctcacctat aaattagagc   2220
ctcggcttca ctctttactc aaaccaaaac tcatcactac agaacataca caagataatt   2280
cgtcgaggat ccgcggccgt cgaatcaaca agtttgtaca aaaaagcagg ctgcggccgc   2340
acaatggctg ccgcgttaca attacaaaca caccccttgct tccatggcac gtgccaactc   2400
tcacctccgc cacgaccttc cgtttccttc ccttcttcct cccgctcgtt tccatctagc   2460
agacgttccc tgtccgcgca tgtgaaggcg gcggcgtcgt ctttgtccac caccaccttg   2520
caggaaggga tagcggagtt ttacgatgag tcgtcgggga tttgggaaga catatggggt   2580
gaccatatgc accatggata ttacgagccg ggttccgata tttcgggttc agatcatcgt   2640
gccgctcaga ttcgaatggt cgaagaatcg ctccgttttg ctggaatatc agaggaccca   2700
gcaaacaggc ccaagagaat agttgatgtt gggtgtggga taggaggcag ttctaggtat   2760
ctagcaagga aatatggggc aaaatgccaa ggcattactt tgagccctgt tcaagctgga   2820
agagccaatg ctcttgctaa tgctcaagga ctagcagaac aggtttgttt tgaagttgca   2880
gatgccttga ccaaccatt ccctgatgac caatttgatc ttgtttggtc tatggaaagc   2940
ggagaacaca tgcctgacaa acccaagttt gttaaagagc tggtgcgagt ggcagctcca   3000
ggaggcacaa taatagtagt gacatggtgc cataggggat ttggtccatc tgaagagtct   3060
ttgcagccat gggagcaaaa gcttttaaac agaatatgtg atgcttacta tttaccagag   3120
tggtgttcta cttctgatta tgtcaaatta tttcagtccc tatctctcca ggatataaag   3180
gcaggagact ggactgagaa tgtagcaccc ttttggccag cagtgatacg ttcagcattg   3240
acatggaagg gcttcacatc gctgctacga agtggattaa aaacaataaa aggtgcactg   3300
gtgatgccat tgatgatcga aggtttccag aaaggggtga taaagtttgc catcattgct   3360
tgccggaagc cagctgagta gcctgcagga cccagctttc ttgtacaaag tggttgatgg   3420
tcgagagtgt gtataccacg gtgatatgag tgtggttgtt gatgtatgtt agcttgggga   3480
caagtttgta caaaaaagca ggctgcggcc gccagtgtga tggatatctg cagaattcgg   3540
cttcgccctt cggccgcgca tgatggtgaa gaaattgtcg acctttctct tgtctgtttg   3600
tcttttgtta aagaagctat gcttcgttct aataatctta ttgtccattt tgttgtgtta   3660
tgacattttg gctgctccca tggcaggtcc gtcgcttctc ttccatttct tctcatttc   3720 gattttgatt cttatttctt tccagtagct cctgctctgt gaatttctcc gctcacgata   3780
gatctgctta tactccttac attcaacctt agatctggtc tcgattctct gtttctctgt   3840
ttttttcttt tggtcgagaa tctgatgttt gtttatgttc tgtcaccatt aataataatg   3900
aactctctca ttcatacaat gattagtttc tctcgtctac aaaacgatat gttgcatttt   3960
cacttttctt ctttttttct aagatgattt gctttgacca atttgtttag atctttattt   4020
tattttattt tctggtgggt tggtggaaat tgaaaaaaaa aaaaacagc ataaattgtt   4080 atttgttaat gtattcattt tttgctatt tgttctgggt aaaaatctgc ttctactatt   4140
gaatctttcc tggattttt actccattg ggtttttata gtaaaaatac ataataaaag   4200
gaaaacaaaa gttttataga ttctcttaaa ccccttacga taaagttgg aatcaaaata   4260 attcaggatc agatgctctt tgattgattc agatgcgatt acagttgcat ggcaaatttt   4320
```

```
ctagatccgt cgtcacattt tattttctgt ttaaatatct aaatctgata tatgatgtcg   4380
acaaattctg gtggcttata catcacttca actgttttct tttggctttg tttgtcaact   4440
tggttttcaa tacgatttgt gatttcgatc gctgaatttt taatacaagc aaactgatgt   4500
taaccacaag caagagatgt gacctgcctt attaacatcg tattacttac tactagtcgt   4560
attctcaacg caatcgtttt tgtatttctc acattatgcc gcttctctac tctttattcc   4620
ttttggtcca cgcatttcct atttgtggca atcccttcca caacctgatt tcccactttg   4680
gatcatttgt ctgaagactc tcttgaatcg ttaccacttg tttcttgtgc atgctctgtt   4740
ttttagaatt aatgataaaa ctattccata gtcttgagtt ttcagcttgt tgattctttt   4800
gcttttggtt ttctgcaggg taccgagcag ccaaaatgtc aaaacacaac aaaatggaca   4860
ataagattat taaaacgaag catagcttct ttaacaaaag acaaacagac aagagaaagg   4920
tcgacaattt cttcaccatc atgccccggg acccagcttt cttgtacaaa gtggtcccca   4980
agctaacact acatagtcat ggtgtgtgtt ccataaataa tgtactaatg taataagaac   5040
tactccgtag acggtaataa aagagaagtt ttttttttta ctcttgctac tttcctataa   5100
agtgatgatt aacaacagat acaccaaaaa gaaaacaatt aatctatatt cacaatgaag   5160
cagtactagt ctattgaaca tgtcagattt tcttttttcta aatgtctaat taagccttca   5220
aggctagtga tgataaaaga tcatccaatg ggatccaaca aagactcaaa tctggttttg   5280
atcagatact tcaaaactat ttttgtattc attaaattat gcaagtgttc ttttatttgg   5340
tgaagactct ttagaagcaa agaacgacaa gcagtaataa aaaaaacaaa gttcagtttt   5400
aagatttgtt attgacttat tgtcatttga aaaatatagt atgatattaa tatagtttta   5460
tttatataat gcttgtctat tcaagatttg agaacattaa tatgatactg tccacatatc   5520
caatatatta agtttcattt ctgttcaaac atatgataag atggtcaaat gattatgagt   5580
tttgttattt acctgaagaa aagataagtg agcttcgagt ttctgaaggg tacgtgatct   5640
tcatttcttg gctaaaagcg aatatgacat cacctagaga aagccgataa tagtaaactc   5700
tgttcttggt ttttggttta atcaaaccga accggtagct gagtgtcaag tcagcaaaca   5760
tcgcaaacca tatgtcaatt cgttagattc ccggtttaag ttgtaaaccg gtatttcatt   5820
tggtgaaaac cctagaagcc agccacccct tttaatctaa ttttttgtaaa cgagaagtca   5880 ccacacctct ccactaaaac cctgaacctt actgagagaa gcagagcgca gctcaaagaa   5940
caaataaaac ccgaagatga gaccaccacg tggcggcggg agcttcaggg gacggggagg   6000
aagagatggc ggcggacgct ttggtggcgg cggcggacgt tttggtggcg gcggtggacg   6060
ttttggtggc ggcggtggac gctttggtgg tggatatcgt gacgaaggac ctcccagtga   6120
agtcattggt tcgtttactc ttttcttagt cgaatcttat tcttgctctg ctcgttgttt   6180
taccgataaa gctaggtaca gcttggcact ggccgtcgtt ttacaacgtc gtgactggga   6240
aaaccctggc gttacccaac ttaatcgcct tgcagcacat ccccctttcg ccagctggcg   6300
taatagcgaa gaggcccgca ccgatcgccc ttcccaacag ttgcgcagcc tgaatggcga   6360
atggcgccaa gctcctcgag ctatctgtca cttcatcaaa aggacagtag aaaaggaagg   6420
tggcacctac aaatgccatc attgcgataa aggaaaggct atcgttcaag atgcctctgc   6480
cgacagtggt cccaaagatg gacccccacc cacgaggagc atcgtggaaa agaagacgt   6540 tccaaccacg tcttcaaagc aagtggattg atgtgatatc tccactgacg taagggatga   6600
cgcacaatcc cactatcctt cgcaagaccc ttcctctata taggaagtt catttcattt    6660 ggagaggaca cgctgaaatc accagtctct ctctacaaat ctatctctct ctattttctc   6720
```

```
cataataatg tgtgagtagt tcccagataa gggaattagg gttcttatag ggtttcgctc    6780
atgagcccag aacgacgccc ggccgacatc cgccgtgcca ccgaggcgga catgccggcg    6840
gtctgcacca tcgtcaacca ctacatcgag acaagcacgg tcaacttccg taccgagccg    6900
caggaaccgc aggagtggac ggacgacctc gtccgtctgc gggagcgcta tccctggctc    6960
gtcgccgagg tggacggcga ggtcgccggc atcgcctacg cgggcccctg gaaggcacgc    7020
aacgcctacg actggacggc cgagtcaacc gtgtacgtct ccccccgcca ccagcggacg    7080
ggactgggct ccacgctcta cacccacctg ctgaagtccc tggaggcaca gggcttcaag    7140
agcgtggttg ctgtcatcgg gctgcccaac gacccgagcg tgcgcatgca cgaggcgctc    7200
ggatatgccc ccgcggcat gctgcgggcg gccggcttca agcacgggaa ctggcatgac    7260
gtgggtttct ggcagctgga cttcagcctg ccagtaccgc cccgtccggt cctgcccgtc    7320
accgagattt gagaattgat cgttcaaaca tttggcaata agtttcttta agattgaatc    7380
ctgttgccgg tcttgcgatg attatcatat aatttctgtt gaattacgtt aagcatgtaa    7440
taattaacat gtaatgcatg acgttatttta tgagatgggt ttttatgatt agagtcccgc    7500
aattatacat ttaatacgcg atagaaaaca aaatatagcg cgcaaactag gataaattat    7560
cgcgcgcggt gtcatctatg ttactagatc ctcgagcgat cgtgaagttt ctcatctaag    7620
cccccatttg gacgtgaatg tagacacgtc gaaataaaga tttccgaatt agaataattt    7680
gtttattgct ttcgcctata aatacgacgg atcgtaattt gtcgttttat caaaatgtac    7740 tttcattta aataacgct gcggacatct acattttga attgaaaaaa aattggtaat    7800
tactctttct tttctccat attgaccatc atactcattg ctgatccatg tagatttccc    7860
ggacatgaag ccatttacaa ttgaatatat cctgccgccg ctgccgcttt gcacccggtg    7920
gagcttgcat gttggtttct acgcagaact gagccggtta ggcagataat ttccattgag    7980
aactgagcca tgtgcacctt cccccaaca cggtgagcga cggggcaacg gagtgatcca    8040
catgggactt ttaaacatca tccgtcggat ggcgttgcga gagaagcagt cgatccgtga    8100
gatcagccga cgcaccgggc aggcgcgcaa cacgatcgca agtatttga acgcaggtac    8160 aatcgagccg acgttcacg                                                 8179

<210> SEQ ID NO 6
<211> LENGTH: 7713
<212> TYPE: DNA
<213> ORGANISM: Artificial Sequence
<220> FEATURE:
<223> OTHER INFORMATION: Vector

<400> SEQUENCE: 6
cgaagctcgg tcccgtgggt gttctgtcgt ctcgttgtac aacgaaatcc attcccattc      60
cgcgctcaag atggcttccc ctcggcagtt catcagggct aaatcaatct agccgacttg     120
tccggtgaaa tgggctgcac tccaacagaa acaatcaaac aaacatacac agcgacttat     180
tcacacgagc tcaaattaca acggtatata tcctgccagt cagcatcatc acaccaaaag     240
ttaggcccga atagtttgaa attagaaagc tcgcaattga ggtctgcgcc caatacgcaa     300
accgcctctc cccgcgcgtt ggccgattca ttaatgcagc tggcacgaca ggtttcccga     360
ctggaaagcg ggcagtgagc gcaacgcaat taatgtgagt tagctcactc attaggcacc     420
ccaggcttta cactttatgc ttccggctcg tatgttgtgt ggaattgtga gcggataaca     480
atttcacaca ggaaacagct atgaccatga ttacgaattg taccgaatta tcactacaat     540
```

```
gtcggagaga caaggctgcg ccagcatata caaaagggaa atgaagatgg cctttttgatt    600
agctgtgtag catcagcagc taatctctgg gctctcatca tggatgctgg aactggattc    660
acttctcaag tttatgagtt gtcaccggtc ttcctacaca aggtaataat cagttgaagc    720
aattaagaat caatttgatt tgtagtaaac taagaagaac ttaccttatg ttttcccgc     780
aggactggat tatggaacaa tgggaaaaga actactatat aagctccata gctggttcag    840
ataacgggag ctcttagtt gttatgtcaa aaggttagtg tttagtgaat aataaactta     900
taccacaaag tcttcattga cttatttata tacttgttgt gaattgctag gaactactta    960
ttctcagcag tcatacaaag tgagtgactc atttccgttc aagtggataa ataagaaatg   1020
gaaagaagat tttcatgtaa cctccatgac aactgctggt aatcgttggg gtgtggtaat   1080
gtcgaggaac tctggcttct ctgatcaggt aggtttttgt ctcttattgt ctggtgtttt   1140
tattttcccc tgatagtcta atatgataaa ctctgcgttg tgaaggtgg tggagcttga    1200
cttttttgtac ccaagcgatg ggatacatag gaggtgggag aatgggtata gaataacatc  1260
aatggcagca actgcggatc aagcagcttt catattaagc ataccaaagc gtaagatggt   1320
ggatgaaact caagagactc tccgcaccac cgcctttcca agtactcatg tcaaggttgg   1380
tttctttagc tttgaacaca gatttggatc ttttttgtttt gtttccatat acttaggacc  1440
tgagagcttt tggttgattt tttttttcagg acaaatgggc gaagaatctg tacattgcat  1500
caatatgcta tggcaggaca gtgtgctgat acacacttaa gcatcatgtg gaaagccaaa   1560
gacaattgga gcgagactca gggtcgtcat aataccaatc aaagacgtaa aaccagacgc   1620
aacctctttg gttgaatgta atgaaaggga tgtgtcttgg tatgtatgta cgaataacaa   1680
aagagaagat ggaattagta gtagaaatat ttgggagctt tttaagcccct tcaagtgtgc  1740
tttttatctt attgatatca tccatttgcg ttgtttaatg cgtctctaga tatgttccta   1800
tatctttctc agtgtctgat aagtgaaatg tgagaaaacc ataccaaacc aaaatattca   1860
aatcttattt ttaataatgt tgaatcactc ggagttgcca ccttctgtgc caattgtgct   1920
gaatctatca cactagaaaa aaacatttct tcaaggtaat gacttgtgga ctatgttctg   1980
aattctcatt aagtttttat tttctgaagt ttaagttttt accttctgtt ttgaaatata   2040
tcgttcataa gatgtcacgc caggacatga gctacacatc gcacatagca tgcagatcag   2100
gacgatttgt cactcacttc aaacacctaa gagcttctct ctcacagcgc acacacatat   2160
gcatgcaata tttacacgtg atcgccatgc aaatctccat tctcacctat aaattagagc   2220
ctcggcttca ctcttttactc aaaccaaaac tcatcactac agaacataca caagataatt  2280
cgtcgaggat ccgcggccgt cgaatcaaca agtttgtaca aaaaagcagg ctgcggccgc   2340
acaatggctg ccgcgttaca attacaaaca caccccttgct tccatggcac gtgccaactc   2400
tcacctccgc cacgaccttc cgtttccttc ccttcttcct cccgctcgtt tccatctagc    2460
agacgttccc tgtccgcgca tgtgaaggcg gcggcgtcgt ctttgtccac caccaccttg   2520
caggaaggga tagcggagtt ttacgatgag tcgtcgggga tttgggaaga catatggggt   2580
gaccatatgc accatggata ttacgagccg ggttccgata tttcgggttc agatcatcgt   2640
gccgctcaga ttcgaatggt cgaagaatcg ctccgttttg ctggaatatc agaggaccca   2700
gcaaacaggc ccaagagaat agttgatgtt gggtgtggga taggaggcag ttctaggtat   2760
ctagcaagga aatatggggc aaaatgccaa ggcattactt tgagccctgt tcaagctgga   2820
agagccaatg ctcttgctaa tgctcaagga ctagcagaac aggtttgttt tgaagttgca   2880
gatgccttga accaaccatt ccctgatgac caatttgatc ttgtttggtc tatggaaagc   2940
```

```
ggagaacaca tgcctgacaa acccaagttt gttaaagagc tggtgcgagt ggcagctcca    3000
ggaggcacaa taatagtagt gacatggtgc catagggatc ttggtccatc tgaagagtct    3060
ttgcagccat gggagcaaaa gcttttaaac agaatatgtg atgcttacta tttaccagag    3120
tggtgttcta cttctgatta tgtcaaatta tttcagtccc tatctctcca ggatataaag    3180
gcaggagact ggactgagaa tgtagcaccc ttttggccag cagtgatacg ttcagcattg    3240
acatggaagg gcttcacatc gctgctacga agtggattaa aaacaataaa aggtgcactg    3300
gtgatgccat tgatgatcga aggtttccag aaagggtga taaagtttgc catcattgct    3360
tgccggaagc cagctgagta gcctgcaggc cgtcgcttct cttccatttc ttctcatttt    3420
cgattttgat tcttatttct ttccagtagc tcctgctctg tgaatttctc cgctcacgat    3480
agatctgctt atactcctta cattcaacct tagatctggt ctcgattctc tgtttctctg    3540 ttttttttctt ttggtcgaga atctgatgtt tgtttatgtt ctgtcaccat taataataat    3600
gaactctctc attcatacaa tgattagttt ctctcgtcta caaaacgata tgttgcattt    3660
tcacttttct tctttttttc taagatgatt tgctttgacc aatttgttta gatctttatt    3720
ttattttatt ttctggtggg ttggtggaaa ttgaaaaaaa aaaaacagc ataaattgtt    3780 atttgttaat gtattcattt tttggctatt tgttctgggt aaaaatctgc ttctactatt    3840
gaatctttcc tggattttt actcctattg gttttttata gtaaaatac ataataaaag    3900 gaaaacaaaa gttttataga ttctcttaaa ccccttacga taaaagttgg aatcaaaata    3960
attcaggatc agatgctctt tgattgattc agatgcgatt acagttgcag ggcaaattttt    4020 ctagatccgt cgtcacattt tatcttctgt ttaaatatct aaatctgata tatgatgtcg    4080
acaaattctg gtggcttata catcacttca actgttttct tttggctttg tttgtcaact    4140
tggttttcaa tacgatctgt gatttcgatc gctgaatttt taatacaagc aaactgatgt    4200
taaccacaag caagagatgt gacctgcctt attaacatcg tattacttac tgctagtcgt    4260
attctcaacg caatcgtttt tgtatttctc acattatgcc gcttctctac tctttattcc    4320
ttttggtcca cgcattttct atttgtggca atccctttca caacctgatt tcccactttg    4380
gatcatttgt ctgaagactc tcttgaatcg ttaccacttg tttcttgtgc atgctctgtt    4440
ttttagaatt aatgataaaa ctattccata gtcttgagtt ttcagcttgt tgattctttt    4500
gcttttggtt ttctgcccaa cactacatag tcatggtgtg tgttccataa ataatgtact    4560
aatgtaataa gaactactcc gtagacggta ataaaagaga agttttttttt tttactcttg    4620 ctactttcct ataaagtgat gattaacaac agatacacca aaagaaaac aattaatcta    4680 tattcacaat gaagcagtac tagtctattg aacatgtcag attttcttttt tctaaatgtc    4740 taattaagcc ttcaaggcta gtgatgataa aagatcatcc aatgggatcc aacaaagact    4800
caaatctggt tttgatcaga tacttcaaaa ctattttttgt attcattaaa ttatgcaagt    4860
gttcttttat ttggtgaaga ctctttagaa gcaagaacg acaagcagta ataaaaaaaa    4920
caaagttcag ttttaagatt tgttattgac ttattgtcat tgaaaaata tagtatgata    4980 ttaatatagt tttatttata taatgcttgt ctattcaaga tttgagaaca ttaatatgat    5040
actgtccaca tatccaatat attaagtttc attctgttc aaacatatga taagatggtc    5100
aaatgattat gagttttgtt atttacctga agaaagata agtgagcttc gagtttctga    5160
agggtacgtg atcttcattt cttggctaaa agcgaatatg acatcaccta gagaaagccg    5220
ataatagtaa actctgttct tggttttgg tttaatcaaa ccgaaccggt agctgagtgt    5280
```

```
caagtcagca aacatcgcaa accatatgtc aattcgttag attcccggtt taagttgtaa    5340
accggtattt catttggtga aaaccctaga agccagccac ccttttaat ctaattttg      5400 taaacgagaa gtcaccacac ctctccacta aaaccctgaa ccttactgag agaagcagag    5460
cgcagctcaa agaacaaata aaacccgaag atgagaccac cacgtggcgg cgggagcttc    5520
aggggacggg gaggaagaga tggcggcgga cgctttggtg gcggcggcgg acgttttggt    5580
ggcggcggtg gacgttttgg tggcggcggt ggacgctttg gtggtggata tcgtgacgaa    5640
ggacctccca gtgaagtcat tggttcgttt actcttttct tagtcgaatc ttattcttgc    5700
tctgctcgtt gttttaccga taaagctagg tacagcttgg cactggccgt cgttttacaa    5760
cgtcgtgact gggaaaaccc tggcgttacc caacttaatc gccttgcagc acatcccct    5820 ttcgccagct ggcgtaatag cgaagaggcc cgcaccgatc gcccttccca acagttgcgc    5880
agcctgaatg gcgaatggcg ccaagctcct cgagctatct gtcacttcat caaaaggaca    5940
gtagaaaagg aaggtggcac ctacaaatgc catcattgcg ataaaggaaa ggctatcgtt    6000
caagatgcct ctgccgacag tggtcccaaa gatggacccc cacccacgag gagcatcgtg    6060
gaaaaagaag acgttccaac cacgtcttca aagcaagtgg attgatgtga tatctccact    6120
gacgtaaggg atgacgcaca atcccactat ccttcgcaag acccttcctc tatataagga    6180
agttcatttc atttggagag gacacgctga aatcaccagt ctctctctac aaatctatct    6240 ctctctatt tctccataat aatgtgtgag tagttcccag ataagggaat tagggttctt     6300
atagggtttc gctcatgagc ccagaacgac gcccggccga catccgccgt gccaccgagg    6360
cggacatgcc ggcggtctgc accatcgtca accactacat cgagacaagc acggtcaact    6420
tccgtaccga gccgcaggaa ccgcaggagt ggacggacga cctcgtccgt ctgcgggagc    6480
gctatccctg gctcgtcgcc gaggtggacg gcgaggtcgc cggcatcgcc tacgcgggcc    6540
cctggaaggc acgcaacgcc tacgactgga cggccgagtc aaccgtgtac gtctccccc     6600 gccaccagcg gacgggactg ggctccacgc tctacaccca cctgctgaag tccctggagg    6660
cacagggctt caagagcgtg gttgctgtca tcgggctgcc caacgacccg agcgtgcgca    6720
tgcacgaggc gctcggatat gccccccgcg gcatgctgcg ggcggccggc ttcaagcacg    6780
ggaactggca tgacgtgggt ttctggcagc tggacttcag cctgccagta ccgcccgtc     6840 cggtcctgcc cgtcaccgag atttgagaat tgatcgttca aacatttggc aataaagttt    6900
cttaagattg aatcctgttg ccggtcttgc gatgattatc atataatttc tgttgaatta    6960
cgttaagcat gtaataatta acatgtaatg catgacgtta tttatgagat gggtttttat    7020
gattagagtc ccgcaattat acatttaata cgcgatagaa acaaaatat agcgcgcaaa     7080 ctaggataaa ttatcgcgcg cggtgtcatc tatgttacta gatcctcgag cgatcgtgaa    7140
gtttctcatc taagcccca tttggacgtg aatgtagaca cgtcgaaata aagatttccg    7200
aattagaata atttgtttat tgctttcgcc tataaatacg acggatcgta atttgtcgtt    7260
ttatcaaaat gtactttcat tttataataa cgctgcggac atctacattt ttgaattgaa    7320
aaaaaattgg taattactct ttcttttct ccatattgac catcatactc attgctgatc     7380
catgtagatt tcccggacat gaagccattt acaattgaat atatcctgcc gccgctgccg    7440
ctttgcaccc ggtggagctt gcatgttggt ttctacgcag aactgagccg gttaggcaga    7500
taatttccat tgagaactga gccatgtgca ccttcccccc aacacggtga gcgacggggc    7560
aacggagtga tccacatggg acttttaaac atcatccgtc ggatggcgtt gcgagagaag    7620
```

```
-continued cagtcgatcc gtgagatcag ccgacgcacc gggcaggcgc gcaacacgat cgcaaagtat      7680
ttgaacgcag gtacaatcga gccgacgttc acg                                  7713
```

COORDINATED DECREASE AND INCREASE OF GENE EXPRESSION OF MORE THAN ONE GENE USING TRANSGENIC CONSTRUCTS

CROSS-REFERENCE TO RELATED APPLICATIONS

This application is a continuation of U.S. application Ser. No. 10/668,240 filed Sep. 24, 2003 now U.S. Pat. No. 7,166,771, which is herein incorporated by reference in its entirety.

INCORPORATION OF SEQUENCE LISTING

A computer readable form of the sequence listing on diskette, containing the file named "P30129US07 SeqList.txt", which is 25,088 bytes in size (measured in Windows XP), and which was created on Dec. 4, 2006, are herein incorporated by reference.

FIELD OF THE INVENTION

The present invention is directed to nucleic acid molecules and nucleic acid constructs, and other agents associated with simultaneous up- and down-regulation of expression of RNAs. Specifically it includes methods of simultaneously enhancing the expression of a first RNA at the same time as suppressing the expression of a second RNA using a single construct. The present invention also specifically provides constructs capable of simultaneously enhancing the expression of a first RNA while at the same time suppressing the expression of a second RNA, methods for utilizing such constructs and plants containing such constructs. The present invention also provides other constructs including polycistronic constructs.

BACKGROUND OF THE INVENTION

Many complex biochemical pathways have now been manipulated genetically, usually by suppression or over-expression of single genes. Further exploitation of the potential for plant genetic manipulation will require the coordinated manipulation of multiple genes in a pathway. A number of approaches have been used to combine transgenes in one plant—including sexual crossing, retransformation, co-transformation, and the use of linked transgenes. A chimeric transgene with linked partial gene sequences can be used to coordinately suppress numerous plant endogenous genes. Constructs modeled on viral polyproteins can be used to simultaneously introduce multiple coding genes into plant cells (for a review, see Halpin et al., *Plant Mol. Biol.* 47:295-310 (2001)).

Enhancement of gene expression in plants may occur through the introduction of extra copies of coding sequences of the genes into a plant cell or, preferably, the incorporation of extra copies of coding sequences of the gene into the plant genome. Over-expression may also occur through increasing the activities of the regulatory mechanisms that regulate the expression of genes, i.e., up-regulation of the gene expression.

Suppression of gene expression, also known as silencing of genes, in plants occurs at both the transcriptional level and post-transcriptional level. There are various methods for the suppression of expression of endogenous sequences in a host cell. Such methods include, but are not limited to, antisense suppression (Smith et al., *Nature* 334:724-726 (1988)), co-suppression (Napoli et al., *Plant Cell* 2:279-289 (1989)), ribozymes (Kohler et al., *J. Mol. Biol.* 285:1935-1950 (1999)), combinations of sense and antisense (Waterhouse et al., *Proc. Natl. Acad. Sci. USA* 95:13959-13964 (1998)), promoter silencing (Park et al., *Plant J.* 9(2):183-194 (1996)), and DNA binding proteins (Beerli et al., *Proc. Natl. Acad. Sci. USA* 95:14628-14633 (1997); Liu et al., *Proc. Natl. Acad. Sci. USA* 94:5525-5530 (1998)).

Certain of these mechanisms are associated with nucleic acid homology at the DNA or RNA level (Matzke et al., *Current Opinion in Genetics and Development* 11:221-227 (2001)). In plants, double-stranded RNA molecules can induce sequence-specific silencing. This phenomenon is often referred to as double stranded RNA ("dsRNA") in plants. This phenomenon has also been reported in *Caenorhabditis elegans*, where this gene-specific silencing is often referred to as RNA interference or RNAi (Fire et al., *Nature* 391:806-811 (1988). Others have reported this phenomenon in plants, fungi and animals (Sharp, *Genes and Development* 13:139-141 (1999); Matzke et al., *Current Opinion in Genetics and Development* 11:221-227 (2001); Cogoni and Macino, *Current Opinion in Genetics and Development* 10:638-643 (2000); Sharp, *Genes and Development* 15:485-490 (2001); Waterhouse et al., *Proc. Natl. Acad. Sci. USA* 95:13959-13964 (1988); Wesley et al., *Plant J.* 27:581-590 (2001); Grierson, WO 98/53083). Wesley et al. reported the design and use of two vectors, pHANNIBAL and pHELLSGATE, that can be used as gene silencing vectors (Wesley et al., supra). These vectors are reported to contain an intron sequence between the sense and antisense sequences where the sense and antisense sequences correspond to a target coding sequence, 5'UTR or 3'UTR. By utilizing a non-target intron between the target sense and antisense sequences, a higher proportion of silenced transformants were obtained (Wesley et al., supra). Another strategy of gene silencing with dsRNA involves a hairpin construct with an intron spacer (Smith et al., *Nature* 407:319-320 (2000)).

Other suppression strategies include, without limitation, antisense and sense suppression. See e.g. Fillatti in PCT WO 01/14538.

A desired plant phenotype may require the expression of one gene and the concurrent reduction of expression of another gene. Thus, there exists a need to simultaneously over-express a polypeptide and suppress, or down-regulate, the expression of a second polypeptide in plants using a single transgenic construct. Moreover, there exists a need to simultaneously suppress or down-regulate the expression of more than one polypeptide using a single construct.

SUMMARY OF THE INVENTION

The present invention includes and provides a nucleic acid molecule comprising a first nucleic acid segment comprising a polypeptide encoding sequence and a second nucleic acid segment comprising a gene suppression sequence, wherein transcription of the nucleic acid molecule in a host cell results in expression of a polypeptide encoded by the polypeptide encoding sequence and suppression of a gene in the host cell.

The present invention includes and provides a plant having a nucleic acid molecule comprising a first nucleic acid segment comprising a polypeptide encoding sequence and a second nucleic acid segment comprising a gene suppression sequence, wherein transcription of the nucleic acid molecule in a host cell results in expression of a polypeptide encoded by the polypeptide encoding sequence and suppression of a gene in the host cell, wherein the first nucleic acid segment and the second nucleic acid segment are operably linked to a single promoter sequence.

The present invention also includes and provides a method of simultaneously altering the expression of more than one RNA molecule comprising introducing into a plant cell a nucleic acid molecule comprising a first nucleic acid segment comprising a polypeptide encoding sequence and a second nucleic acid segment comprising a gene suppression sequence, wherein transcription of the nucleic acid molecule in a host cell results in expression of a polypeptide encoded by the polypeptide encoding sequence and suppression of a gene in the host cell, wherein the first nucleic acid segment and the second nucleic acid segment are operably linked to a single promoter sequence, and the first nucleic acid segment and the second nucleic acid segment are expressed.

DETAILED DESCRIPTION OF THE INVENTION

Description of Nucleic Acid Sequences

Figure 1:
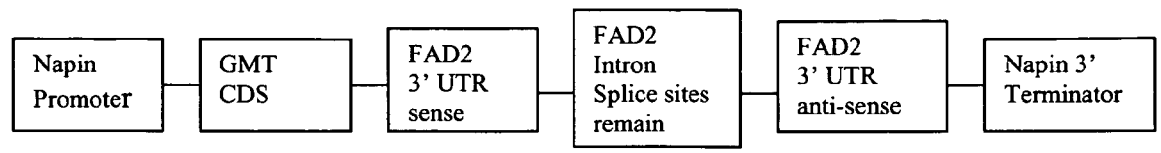
FIG. 1 is a schematic of DNA construct elements in vector pMON75565.

SEQ ID NO: 1 sets forth a nucleic acid sequence of a DNA molecule that encodes a *Gossypium hirsutum* gamma-tocopherol methyltransferase.

SEQ ID NOs: 2 and 3 set forth nucleic acid sequences of primers for use in amplifying a *Gossypium hirsutum* gamma methyl transferase.

SEQ ID NO: 4 is the 1405 nucleotide long DNA sequence of the RNAi operative element found at bases 3345-4947 of pMON75565. SEQ ID NO:4 comprises in 5' to 3' direction a sense-oriented 3'UTR sequence from *Arabidopsis thaliana* FAD2 (bases 1-135) linked to a sense-oriented intron sequence with splice sites removed from *Arabidopsis thaliana* FAD2 (bases 144-1275) linked to an antisense oriented 3'UTR sequence from *Arabidopsis thaliana* FAD2 (bases 1281-1405). FAD2 intron elements essentially as in SEQ ID NO:4 are found within pMON75565 at bases 3687-4818 and within SEQ ID:5 at bases 3396-4515.

SEQ ID NO:5 is the 8179 nucleotide long DNA sequence of the transformation insertion element between *Agrobacterium tumefaciens* border elements from vector pMON75565, i.e. the elements of a first transcription unit for simultaneously increasing expression of GMT and decreasing expression of Δ12 desaturase by RNAi and a second transcription unit for a BAR marker.

SEQ ID NO:6 is the 7713 nucleotide long DNA sequence of the transformation insertion element between *Agrobacterium tumefaciens* border elements from vector pMON75571, i.e. the elements of a first transcription units for simultaneously increasing expression of GMT and decreasing expression of Δ12 desaturase by intron sense suppression and a second transcription unit for a BAR marker.

DEFINITIONS

As used herein, "gene" refers to a nucleic acid sequence that encompasses a 5' promoter region associated with the expression of the gene product, any intron and exon regions and 3' untranslated regions ("UTR") associated with the expression of the gene product.

As used herein, "a transgenic plant" is any plant that stably incorporates a transgene in a manner that facilitates transmission of that transgene from a plant by any sexual or asexual method.

As used herein, "transgene" refers to a nucleic acid sequence associated with the expression of a gene introduced to a cell of an organism. A transgene includes, but is not limited to, a gene endogenous to or a gene not naturally occurring in the organism.

As used herein, "gene silencing" or "suppression" refers to the down-regulation of gene expression by any method including, without limitation, antisense suppression, sense suppression and sense intron suppression. Such down-regulation can be a partial down-regulation.

As used herein, "a gene suppression sequence" is any nucleic acid sequence capable, when transcribed, of down-regulating gene expression. Such methods include but are not limited to antisense suppression, sense suppression and sense intron suppression.

As used herein, "antisense suppression" refers to gene silencing that is induced by the introduction of an antisense RNA molecule.

As used herein, "sense suppression" refers to gene silencing that is induced by the introduction of a fragment of a gene in the sense orientation including, without limitation, a coding region or fragment thereof.

As used herein, "sense intron suppression" refers to gene silencing that is induced by the introduction of a intron in the sense orientation or fragment thereof of a gene. Sense intron suppression is described by Fillatti in PCT WO 01/14538 A2, the entirety of which is incorporated herein by reference.

When referring to proteins and nucleic acids herein, the use of plain capitals, e.g., "GMT" or "FAD2," indicates a reference to an enzyme, protein, polypeptide, or peptide, and the use of italicized capitals, e.g., "*GMT*" or "*FAD2*," refers to nucleic acids, including without limitation, genes, cDNAs, and mRNAs.

When referring to agents such as proteins and nucleic acids herein, "derived" refers to obtaining a protein or nucleic acid from a known protein or nucleic acid either directly (for example, by looking at the sequence of a known protein or nucleic acid and preparing a protein or nucleic acid having a sequence similar, at least in part, to the sequence of the known protein or nucleic acid) or indirectly (for example, by obtaining a protein or nucleic acid from an organism which is related to a known protein or nucleic acid). Other methods of "deriving" a protein or nucleic acid from a known protein or nucleic acid are known to one of skill in the art.

When referring to nucleic acid constructs herein, it is understood that the construct may be in linear or circular form.

As used herein, "a nucleic acid segment" is a portion of a larger nucleic acid molecule. Such nucleic acid segments can, for example, without limitation, comprise a polypeptide encoding sequence or a gene suppression sequence or both.

As used herein, "RNAi," and "dsRNA," refer to gene silencing that is induced by the introduction of a double-stranded RNA molecule.

As used herein, a "dsRNA molecule" and an "RNAi molecule" both refer to a double-stranded RNA molecule capable, when introduced into a cell or organism, of at least partially reducing the level of an mRNA species present in a cell or a cell of an organism.

As used herein, an "intron dsRNA molecule" and an "intron RNAi molecule" both refer to a double-stranded RNA molecule capable, when introduced into a cell or organism, of at least partially reducing the level of an mRNA species present in one or more cells where the double-stranded RNA molecule exhibits sufficient identity to an intron of a gene present in the cell or organism to reduce the level of an mRNA containing that intron sequence.

The term "non-coding" refers to sequences of nucleic acid molecules that do not encode part or all of an expressed protein. Non-coding sequences include but are not limited to introns, promoter regions, 3' untranslated regions ("3'UTR"), and 5' untranslated regions ("5'UTR").

The term "intron" as used herein refers to the normal sense of the term as meaning a segment of a nucleic acid molecule, usually DNA, that does not encode part of or all of an expressed protein, and which, in endogenous conditions, is transcribed into RNA molecules, but which is spliced out of the endogenous RNA before the RNA is translated into a protein.

The term "exon" as used herein refers to the normal sense of the term as meaning a segment of nucleic acid molecules, usually DNA, which encodes part of or all of an expressed protein.

As used herein, a promoter that is "operably linked" to one or more nucleic acid sequences is capable of driving expression of one or more nucleic acid sequences, including multiple coding or non-coding nucleic acid sequences arranged in a polycistronic configuration or construct.

As used herein, a "plant promoter" includes, without limitation, a plant viral promoter and a synthetic, chimeric or hybrid promoter, which is a single transcriptional unit, capable of functioning in a plant cell to promote the expression of an mRNA.

A "polycistronic configuration" or "polycistronic construct" is a configuration which comprises nucleic acid sequences of more than one gene. It is understood that within a "polycistronic configuration" there may be sequences that correspond to exons, introns or both, and a "polycistronic configuration" might, for example without limitation, contain sequences that correspond to one or more exons from one gene and one or more introns from a second gene.

As used herein, a "polycistronic gene" or "polycistronic mRNA" is any gene or mRNA that contains nucleic acid sequences which correspond to nucleic acid sequences of more than one gene. It is understood that such polycistronic genes or mRNAs may contain sequences that correspond to exons, introns or both and that a recombinant polycistronic gene or mRNA might, for example without limitation, contain sequences that correspond to one or more exons from one gene and one or more introns from a second gene.

As used herein, "physically linked" nucleic acid sequences are nucleic acid sequences that are found on a single nucleic acid molecule.

As used herein, "expression" refers to the process of transcription and translation.

As used herein, "simultaneous expression" of more than one agent such as an mRNA or protein refers to the expression of an agent at the same time as another agent. Such expression may only overlap in part and may also occur in different tissues or at different levels.

As used herein, "simultaneously altering expression" of more than one agent such as an mRNA or protein refers to altering the expression of an agent at the same time as altering the expression of another agent. Such expression of the more than one agent may be altered in different tissues or at different levels.

As used herein, "coexpression" of more than one agent such as an mRNA or protein refers to the simultaneous expression of an agent at the same time and in the same cell or tissue as another agent.

As used herein, "coordinated expression" of more than one agent" refers to the coexpression of more than one agent when the expression of such agents is carried out utilizing a shared or identical promoter.

As used herein, an "at least partially enhanced" or an "increased" level of an agent such as a protein or mRNA is at least partially enhanced or increased if the level of that agent is increased relative to the level that that agent is present in a cell, tissue, plant or organism with a similar genetic background but lacking an introduced nucleic acid molecule encoding the protein or mRNA.

As used herein, a "polypeptide" comprises fifteen or greater amino acid residues.

As used herein, a "peptide" contains 14 or fewer amino acid residues.

As used herein, an "enhanced" level of an agent such as a protein, polypeptide, peptide, or mRNA is enhanced if the level of that agent is increased at least 25% relative to the level that that agent is present in a cell, tissue, plant or organism with a similar genetic background but lacking an introduced nucleic acid molecule encoding the protein or mRNA.

As used herein, the level of an agent such as a protein, polypeptide, peptide, or mRNA is "substantially enhanced" if the level of that agent is increased at least 75% relative to the level that that agent is present in a cell, tissue, plant or organism with a similar genetic background but lacking an introduced nucleic acid molecule encoding the protein or mRNA.

As used herein, "a reduction" of the level of an agent such as a protein, polypeptide, peptide, or mRNA means that the level is decreased relative to a cell, tissue, plant or organism with a similar genetic background but lacking a nucleic acid sequence capable of reducing the agent.

As used herein, "at least a partial reduction" of the level of an agent such as a protein, polypeptide, peptide, or mRNA means that the level is decreased at least 25% relative to a cell, tissue, plant or organism with a similar genetic background but lacking a nucleic acid sequence capable of reducing the agent.

As used herein, "a substantial reduction" of the level of an agent such as a protein, polypeptide, peptide, or mRNA means that the level is decreased relative to a cell, tissue, plant or organism with a similar genetic background but lacking a nucleic acid sequence capable of reducing the agent, where the decrease in the level of the agent is at least 75%.

As used herein, "an effective elimination" of an agent such as a protein, polypeptide, peptide, or mRNA is relative to a cell, tissue, plant or organism with a similar genetic background but lacking a nucleic acid sequence capable of decreasing the agent, where the decrease in the level of the agent is greater than 95%.

As used herein, "heterologous" means not naturally occurring together.

As used herein, "an endogenous gene" is any gene that is not introduced into a host by transformation or transfection.

As used herein, "total oil level" refers to the total aggregate amount of fatty acid without regard to the type of fatty acid.

As used herein, an "altered seed oil composition" refers to a seed composition in which the relative percentages of the types of fatty acids are altered.

As used herein, any range set forth is inclusive of the end points of the range unless otherwise stated.

Agents of the invention will preferably be "biologically active" with respect to either a structural attribute, such as the capacity of a nucleic acid molecule to hybridize to another nucleic acid molecule, or the ability of a protein to be bound by an antibody (or to compete with another molecule for such binding). Alternatively, such biological activity may be catalytic and thus involve the capacity of the agent to mediate a chemical reaction or response.

Agents will preferably be "substantially purified." The term "substantially purified," as used herein, refers to a molecule separated from substantially all other molecules normally associated with it in its native environmental conditions. More preferably a substantially purified molecule is the predominant species present in a preparation. A substantially purified molecule may be greater than 60% free, greater than 75% free, preferably greater than 90% free, and most preferably greater than 95% free from the other molecules (exclusive of solvent) present in the natural mixture. The term "substantially purified" is not intended to encompass molecules present in their native environmental conditions.

Agents of the invention may also be recombinant. As used herein, the term "recombinant" means any agent (e.g., including but not limited to DNA, RNA, peptide), that is, or results, however indirectly, from human manipulation of a nucleic acid molecule or peptide.

Agents of the invention may be labeled with reagents that facilitate detection of the agent (e.g., fluorescent labels, Prober et al., *Science* 238:336-340 (1987); Albarella et al., EP 144914; chemical labels, Sheldon et al., U.S. Pat. No. 4,582,789; Albarella et al., U.S. Pat. No. 4,563,417; modified bases, Miyoshi et al., EP 119448).

As used herein, "% identity" is determined using the following parameters and algorithm: Smith Waterman algorithm is used to determine identity. Parameters for polypeptide sequence comparison typically include the following: Algorithm: Needleman and Wunsch, *J. Mol. Biol.* 48:443-453 (1970). Comparison matrix: BLOSSUM62 from Hentikoff and Hentikoff, *Proc. Natl. Acad. Sci. USA* 89:10915-10919 (1992). Gap Penalty: 12; Gap Length Penalty: 4. A program that can be used with these parameters is publicly available as the "gap" program from Genetics Computer Group ("GCG"), Madison, Wis. The above parameters along with no penalty for end gap are the default parameters for peptide comparisons. Parameters for nucleic acid molecule sequence comparison are the following: Algorithm: Needleman and Wunsch, *J. Mol. Bio.* 48:443-453 (1970). Comparison matrix: matches—+10, mismatches=0; Gap Penalty: 50; Gap Length Penalty: 3. "% identity" is determined using the above parameters as the default parameters for nucleic acid molecule sequence comparisons and the "gap" program from GCG, version 10.2.

As used herein, a gamma-tocopherol methyltransferase (also referred to as GMT, γ-GMT, γ-MT, γ-TMT or gamma-methyltransferase) is any polypeptide that is capable of specifically catalyzing the conversion of γ-tocopherol into α-tocopherol. In certain plant species such as soybean, GMT can also catalyze the conversion of δ-tocopherol to β-tocopherol. In other plants, GMT, can also catalyze the conversion of δ-tocotrienol to β-tocotrienol.

As used herein, a "FAD2", "Δ12 desaturase" or "omega-6 desaturase" gene is a gene that encodes an enzyme capable of catalyzing the insertion of a double bond into a fatty acyl moiety at the twelfth position counted from the carboxyl terminus.

Nucleic Acid Molecules, Constructs and Vectors

Vector systems suitable for introducing transforming DNA into a host plant cell include, but are not limited to, binary bacterial artificial chromosome (BIBAC) vectors (Hamilton et al., *Gene* 200:107-116 (1997)); RNA viral vectors (Della-Cioppa et al., *Ann. N.Y. Acad. Sci.* 792 (Engineering Plants for Commercial Products and Applications):57-61 (1996)); plant selectable YAC (Yeast Artificial Chromosome) vectors such as those described in Mullen et al., *Molecular Breeding* 4:449-457 (1988); cosmids; and bacterial artificial chromosomes (BACs), and such vector systems can be utilized with nucleic acid molecules of the present invention. In one aspect of the invention such vectors contain a nucleic acid molecule comprising a first nucleic acid segment comprising a polypeptide encoding sequence and a second nucleic acid segment comprising a gene suppression sequence, wherein transcription of said nucleic acid molecule in a host cell results in expression of a polypeptide encoded by the polypeptide encoding sequence and suppression of a gene in the host cell. In one aspect, the first nucleic acid and the second nucleic acid segment are operably linked to a single promoter sequence. A second nucleic acid segment may be expressed, for example, without limitation, as a dsRNA molecule, an RNAi molecule, an intron dsRNA molecule, or an intron RNAi molecule. In an aspect of the present invention, such first nucleic acid segment and second nucleic acid segment can be expressed, coexpressed, or coordinately expressed in a host cell and, upon expression, the RNA encoded by the second nucleic acid segment is suppressed.

A. Promoter

In an aspect of the present invention, nucleic acid molecules, constructs or vectors contain a promoter that is operably linked to one or more nucleic acid sequences. Any promoter that functions in a plant cell to cause the production of an mRNA molecule, such as those promoters described herein, without limitation, can be used. In a preferred embodiment, the promoter is a plant promoter.

A number of promoters that are active in plant cells have been described in the literature. These include, but are not limited to, the nopaline synthase (NOS) promoter (Ebert et al., *Proc. Natl. Acad. Sci. USA* 84:5745-5749 (1987)), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., *Plant Mol. Biol.* 9:315-324 (1987)), and the CaMV 35S promoter (Odell et al., *Nature* 313:810-812 (1985)), the figwort mosaic virus 35S-promoter (U.S. Pat. No. 5,378,619), the light-inducible promoter from the small subunit of ribulose-1,5-bis-phosphate carboxylase (ssRUBISCO), the Adh promoter (Walker et al., *Proc. Natl. Acad. Sci. USA* 84:6624-6628 (1987)), the sucrose synthase promoter (Yang et al., *Proc. Natl. Acad. Sci. USA* 87:4144-4148 (1990)), the R gene complex promoter (Chandler et al., *Plant Cell* 1:1175-1183 (1989)) and the chlorophyll a/b binding protein gene promoter. These promoters have been used to create DNA constructs that have been expressed in plants (See, e.g., PCT WO 84/02913). The CaMV 35S promoters are preferred for use in plants. See also U.S. Pat. No. 6,437,217, which discloses a maize RS81 promoter; U.S. Pat. No. 5,641,876, which discloses a rice actin promoter; U.S. Pat. No. 6,426,446, which discloses a maize RS324 promoter; U.S. Pat. No. 6,429,362, which discloses a maize PR-1 promoter; U.S. Pat. No. 6,232,526, which discloses a maize A3 promoter; and U.S. Pat. No. 6,177,611, which discloses constitutive maize promoter, all of which are incorporated by reference. The rice actin 1 promoter with a rice actin intron is especially useful in the practice of the present invention.

Particularly preferred promoters can also be used to express a nucleic acid molecule of the present invention in seeds or fruits. Indeed, in a preferred embodiment, the promoter used is a seed specific promoter. Examples of such promoters include the 5' regulatory regions from such genes as napin (Kridl et al., *Seed Sci. Res.* 1:209:219 (1991)), phaseolin (Bustos et al., *Plant Cell* 1(9):839-853 (1989)), soybean trypsin inhibitor (Riggs et al., *Plant Cell* 1(6):609-621 (1989)), ACP (Baerson et al., *Plant Mol. Biol.* 22(2):255-267 (1993)), stearoyl-ACP desaturase (Slocombe et al., *Plant Physiol.* 104(4): 167-176 (1994)), soybean a' subunit of b-conglycinin (soy 7s promoter, (Chen et al., *Proc. Natl. Acad. Sci. USA* 83:8560-8564 (1986))), fatty acid elongation (FAE1) promoter (PCT WO 01/11061), and oleosin (see, for example, Hong et al., *Plant Mol. Biol.* 34(3):549-555 (1997)). Further examples include the promoter for β-conglycinin (Chen et al., *Dev. Genet.* 10: 112-122 (1989)). Preferred promoters for expression in the seed are 7S and napin promoters.

Also included are the zein promoters, which are a group of storage proteins found in corn endosperm. Genomic clones for zein genes have been isolated (Pedersen et al., *Cell* 29:1015-1026 (1982); Russell et al., *Transgenic Res.* 6(2): 157-168 (1997)) and the promoters from these clones, including the 15 kD, 16 kD, 19 kD, 22 kD, and 27 kD genes, could also be used. Other promoters known to function, for example in corn, include the promoters for the following genes: waxy, Brittle, Shrunken 2, Branching enzymes I and II, starch synthases, debranching enzymes, oleosins, glutelins and sucrose synthases. A particularly preferred promoter for corn endosperm expression is the promoter for the glutelin gene from rice, more particularly the Osgt-1 promoter (Zheng et al., *Mol. Cell Biol.* 13:5829-5842 (1993)). Examples of promoters suitable for expression in wheat include those promoters for the ADP glucose pyrosynthase (ADPGPP) subunits, the granule bound and other starch synthase, the branching and debranching enzymes, the embryogenesis-abundant proteins, the gliadins and the glutenins. Examples of such promoters in rice include those promoters for the ADPGPP subunits, the granule bound and other starch synthase, the branching enzymes, the debranching enzymes, sucrose synthases and the glutelins. A particularly preferred promoter is the promoter for rice glutelin, Osgt-1. Examples of such promoters for barley include those for the ADPGPP subunits, the granule bound and other starch synthase, the branching enzymes, the debranching enzymes, sucrose synthases, the hordeins, the embryo globulins and the aleurone specific proteins.

Tissue-specific expression of a protein of the present invention is a particularly preferred embodiment. The tissue-specific promoters that can be used include the chloroplast glutamine synthetase GS2 promoter from pea (Edwards et al., *Proc. Natl. Acad. Sci. USA* 87:3459-3463 (1990)), the chloroplast fructose-1,6-biphosphatase (FBPase) promoter from wheat (Lloyd et al., *Mol. Gen. Genet.* 225:209-216 (1991)), the nuclear photosynthetic ST-LS1 promoter from potato (Stockhaus et al., *EMBO J.* 8:2445-2451 (1989)), the serine/threonine kinase (PAL) promoter and the glucoamylase (CHS) promoter from *Arabidopsis thaliana*. Also reported to be active in photosynthetically active tissues are the ribulose-1,5-bisphosphate carboxylase (rbcS) promoter from eastern larch (*Larix laricina*), the promoter for the cab gene, cab6, from pine (Yamamoto et al., *Plant Cell Physiol.* 35:773-778 (1994)), the promoter for the Cab-1 gene from wheat (Fejes et al., *Plant Mol. Biol.* 15:921-932 (1990)), the promoter for the CAB-1 gene from spinach (Lubberstedt et al., *Plant Physiol.* 104:997-1006 (1994)), the promoter for the cab1R gene from rice (Luan et al., *Plant Cell* 4:971-981 (1992)), the pyruvate, orthophosphate dikinase (PPDK) promoter from corn (Matsuoka et al., *Proc. Natl. Acad. Sci. USA* 90: 9586-9590 (1993)), the promoter for the tobacco Lhcb1*2 gene (Cerdan et al., *Plant Mol. Biol.* 33:245-255 (1997)), the *Arabidopsis thaliana* SUC2 sucrose-H+ symporter promoter (Truernit et al., *Planta.* 196:564-570 (1995)) and the promoter for the thylakoid membrane proteins from spinach (psaD, psaF, psaE, PC, FNR, atpC, atpD, cab, rbcS). Other promoters for the chlorophyll a/b-binding proteins may also be utilized in the invention, such as the promoters for LhcB gene and PsbP gene from white mustard (Sinapis alba; Kretsch et al., *Plant Mol. Biol.* 28:219-229 (1995)).

A number of promoters for genes with tuber-specific or tuber-enhanced expression are known and can be used, including the class I patatin promoter (Bevan et al., *EMBO J.* 8:1899-1906 (1986); Jefferson et al., *Plant Mol. Biol.* 14:995-1006 (1990)), the promoter for the potato tuber ADPGPP genes, both the large and small subunits, the sucrose synthase promoter (Salanoubat and Belliard, *Gene* 60:47-56 (1987), Salanoubat and Belliard, *Gene* 84:181-185 (1989)), the promoter for the major tuber proteins including the 22 kd protein complexes and protease inhibitors (Hannapel, *Plant Physiol.* 101:703-704 (1993)), the promoter for the granule-bound starch synthase gene (GBSS) (Visser et al., *Plant Mol. Biol.* 17:691-699 (1991)) and other class I and II patatins promoters (Koster-Topfer et al., *Mol. Gen. Genet.* 219:390-396 (1989); Mignery et al., *Gene.* 62:27-44 (1988)).

Root specific promoters may also be used. An example of such a promoter is the promoter for the acid chitinase gene (Samac et al., *Plant Mol. Biol.* 25:587-596 (1994)). Expression in root tissue could also be accomplished by utilizing the root specific subdomains of the CaMV35S promoter that have been identified (Lam et al., *Proc. Natl. Acad. Sci. USA* 86:7890-7894 (1989)). Other root cell specific promoters include those reported by Conkling et al. (Conkling et al., *Plant Physiol.* 93:1203-1211 (1990)).

The promoters used in the nucleic acid constructs of the present invention may be modified, if desired, to affect their control characteristics. Promoters can be derived by means of ligation with operator regions, random or controlled mutagenesis, etc. Furthermore, the promoters may be altered to contain multiple "enhancer sequences" to assist in elevating gene expression. Such enhancers are known in the art. By including an enhancer sequence with such constructs, the expression of the selected protein may be enhanced. These enhancers often are found 5' to the start of transcription in a promoter that functions in eukaryotic cells, but can often be inserted in the forward or reverse orientation 5' or 3' to the coding sequence. In some instances, these 5' enhancing elements are introns. Deemed to be particularly useful as enhancers are the 5' introns of the rice actin 1 and rice actin 2 genes. Examples of other enhancers which could be used in accordance with the invention include elements from the CaMV 35S promoter, octopine synthase genes, the maize alcohol dehydrogenase gene, the maize shrunken 1 gene and promoters from non-plant eukaryotes.

Where an enhancer is used in conjunction with a promoter for the expression of a selected protein, it is believed that it will be preferred to place the enhancer between the promoter and the start codon of the selected coding region. However, one also could use a different arrangement of the enhancer relative to other sequences and still realize the beneficial properties conferred by the enhancer. For example, the enhancer could be placed 5' of the promoter region, within the promoter region, within the coding sequence (including within any other intron sequences which may be present), or 3' of the coding region.

In addition to introns with enhancing activity, other types of elements can influence gene expression. For example, untranslated leader sequences predicted to enhance gene expression as well as "consensus" and preferred leader sequences have been identified. Preferred leader sequences are contemplated to include those which have sequences predicted to direct optimum expression of the attached coding region, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants, and in maize in particular, will be most preferred. For example, sequences derived from the small subunit of ribulose bisphosphate carboxylase (RUBISCO).

In general it is preferred to introduce heterologous DNA randomly, i.e. at a non-specific location, in the genome. In special cases it may be useful to target heterologous nucleic acid insertion in order to achieve site specific integration, e.g. to replace an existing gene in the genome. In some other cases it may be useful to target a heterologous nucleic acid integration into the genome at a predetermined site from which it is known that gene expression occurs. Several site specific recombination systems exist which are known to function in plants including cre-lox as disclosed in U.S. Pat. No. 4,959,317 and FLP-FRT as disclosed in U.S. Pat. No. 5,527,695.

Additional promoters that may be utilized are described, for example, in U.S. Pat. Nos. 5,378,619; 5,391,725; 5,428,147; 5,447,858; 5,608,144; 5,614,399; 5,633,441; 5,633,435; and 4,633,436. In addition, a tissue specific enhancer may be used (Fromm et al., *Plant Cell* 1:977-984 (1989)).

B. Nucleic Acid Molecules

In an aspect of the invention, the nucleic acid molecule comprises a nucleic acid sequence, which when introduced into a cell or organism, is capable of simultaneously overexpressing, expressing, coexpressing or coordinately expressing one or more RNA molecules to produce one or more proteins, fragments thereof, polypeptides, or peptides while expressing one or more other RNA molecules capable of suppressing the level of one or more RNA molecules expressed in the cell or organism.

In this aspect of the present invention any protein, fragment thereof, polypeptide, or peptide can be expressed and any RNA molecule can be suppressed. Nucleic acid sequences encoding such proteins, fragments thereof, polypeptides, and peptides as well as nucleic acid sequences useful in the suppression of one or more mRNA molecules expressed in the cell or organism can be derived, for example, without limitation, from a gene, fragment thereof, cDNA, fragment thereof, etc.

A gene of the present invention can be any gene, whether endogenous or introduced. Nucleic acid sequences of such genes can be derived from a multitude of sources, including, without limitation, databases such as EMBL and Genbank found on the Worldwide web at ebi.ac.uk/swisprot/, expasy.ch/, embl.heidelberg.de/, and ncbi.nlm.nih.gov. Nucleic acid sequences of such genes can also be derived, without limitation, from sources such as the GENSCAN program found at the website genes.mit.edu/GENSCAN.html.

In a further embodiment, additional genes may be obtained by any method by which additional genes may be identified. In a preferred embodiment, an additional gene may be obtained by screening a genomic library with a probe of known gene sequences. The gene may then be cloned and confirmed. Additional genes may, for example without limitation, be amplified by polymerase chain reaction (PCR) and used in an embodiment of the present invention. In addition, other nucleic acid sequences of genes will be apparent to one of ordinary skill in the art.

Any of a variety of methods may be used to obtain one or more genes. Automated nucleic acid synthesizers may be employed for this purpose, and to make a nucleic acid molecule that has a sequence also found in a cell or organism. In lieu of such synthesis, nucleic acid molecules may be used to define a pair of primers that can be used with the PCR to amplify and obtain any desired nucleic acid molecule or fragment of a first gene.

In a preferred aspect, the gene, mRNA or protein is a non-viral gene, mRNA or protein. In another preferred aspect, the gene, RNA or protein is an endogenous gene, RNA or protein. In a preferred aspect, a gene is a GMT gene. A preferred GMT gene of the present invention is a plant or cyanobacterial GMT, more preferably a GMT that is also found in an organism selected from the group consisting of *Arabidopsis*, rice, corn, cotton, cuphea, oilseed rape, tomato, soybean, marigold, sorghum, and leek, most preferably a GMT that is also found in an organism selected from the group consisting of *Arabidopsis thaliana, Oryza sativa, Zea mays, Gossypium hirsutum, Cuphea pulcherrima, Brassica napus, Lycopersicon esculentum, Glycine max, Tagetes erecta,* and *Lilium asiatic.* Representative sequences for GMT genes include, without limitation, those set forth in U.S. patent application Ser. No. 10/219,810, filed on Aug. 16, 2002.

In an aspect, another preferred gene of the present invention is a FAD2 gene. Representative sequences for FAD2 include, without limitation, those set forth in U.S. application Ser. No. 10/176,149, filed Jun. 21, 2002, and U.S. patent application Ser. No. 09/638,508, filed Aug. 11, 2000, and U.S. Provisional Application Ser. No. 60/151,224, filed Aug. 26, 1999, and U.S. Provisional Application Ser. No. 60/172,128, filed Dec. 17, 1999. In a preferred aspect a GMT protein is expressed and the expression of a FAD2 protein is suppressed.

In an aspect of the present invention, a nucleic acid molecule comprising a first nucleic acid segment comprising a polypeptide encoding sequence and a second nucleic acid segment comprising a gene suppression sequence, wherein transcription of the nucleic acid molecule in a host cell results in expression of a polypeptide encoded by the polypeptide encoding sequence and suppression of a gene in said host cell, where the first nucleic acid segment and the second nucleic acid segment are operably linked to a single promoter sequence.

In a preferred aspect of the present invention the nucleic acid molecule further comprises nucleotide sequences encoding a plastid transit peptide operably fused to a nucleic acid molecule of the present invention that encodes a protein, fragment thereof, polypeptide, or peptide.

A nucleic acid molecule or protein, fragment thereof, polypeptide, or peptide of the present invention may differ in either nucleic acid or amino acid sequence from a gene or its translated product but nonetheless share a percentage identity with a nucleic acid or amino acid sequence from a gene. "Identity," as is well understood in the art, is a relationship between two or more polypeptide sequences or two or more nucleic acid molecule sequences, as determined by comparing the sequences. In the art, "identity" also means the degree of sequence relatedness between polypeptide or nucleic acid molecule sequences, as determined by the match between strings of such sequences. "Identity" can be readily calculated by known methods.

In another aspect, the nucleic acid sequence of the nucleic acid molecules of the present invention can comprise sequences that differ from those encoding a protein, fragment thereof, polypeptide, or peptide due to the fact that a protein, fragment thereof, polypeptide, or peptide can have one or more conservative amino acid changes, and nucleic acid sequences coding for the polypeptide can therefore have sequence differences.

It is well known in the art that one or more amino acids in a native sequence can be substituted with other amino acid(s), the charge and polarity of which are similar to that of the native amino acid, i.e., a conservative amino acid substitution. Hydropathic index of amino acids may also be considered when making amino acid changes. The importance of the hydropathic amino acid index in conferring interactive biological function on a protein is generally understood in the art (Kyte and Doolittle, J. Mol. Biol. 157:105-132 (1982)). It is also understood in the art that the substitution of like amino acids can be made effectively on the basis of hydrophilicity. U.S. Pat. No. 4,554,101 states that the greatest local average hydrophilicity of a protein, as governed by the hydrophilicity of its adjacent amino acids, correlates with a biological property of the protein. In making such changes, the substitution of amino acids whose hydrophilicity values are within ±2 is preferred, those that are within ±1 are particularly preferred, and those within ±0.5 are even more particularly preferred.

Due to the degeneracy of the genetic code, different nucleotide codons may be used to code for a particular amino acid. A host cell often displays a preferred pattern of codon usage. Structural nucleic acid sequences are preferably constructed to utilize the codon usage pattern of the particular host cell. This generally enhances the expression of the structural nucleic acid sequence in a transformed host cell. Any of the above-described nucleic acid and amino acid sequences may be modified to reflect the preferred codon usage of a host cell or organism in which they are contained. Modification of a structural nucleic acid sequence for optimal codon usage in plants is described in U.S. Pat. No. 5,689,052.

Preferred embodiments of the invention include nucleic acid molecules that comprise a first, second or both nucleic acid segment(s), which is at least 50%, 60%, or 70% identical over its entire length to a plant gene. More preferable are first, second or both nucleic acid segments which comprise a region that is at least 80% or at least 85% identical over its entire length to a plant gene. In this regard first and second nucleic acid segments at least 90% identical over their entire length are particularly preferred, those at least 95% identical are especially preferred. Further, those with at least 97% identity are highly preferred and those with at least 98% and at least 99% identity are particularly highly preferred, with those exhibiting 100% identity being the most highly preferred.

A subset of the first or second nucleic acid segment of the nucleic acid molecules of the invention includes fragment nucleic acid molecules. Fragment nucleic acid molecules may consist of significant portion(s) of, or indeed most of, a plant gene. Alternatively, fragments may comprise smaller oligonucleotides, having from about 15 to about 400 contiguous nucleotide residues and more preferably, about 15 to about 45 contiguous nucleotide residues, about 20 to about 45 contiguous nucleotide residues, about 15 to about 30 contiguous nucleotide residues, about 21 to about 30 contiguous nucleotide residues, about 21 to about 25 contiguous nucleotide residues, about 21 to about 24 contiguous nucleotide residues, about 19 to about 25 contiguous nucleotide residues, or about 21 contiguous nucleotides. In a preferred embodiment, a fragment shows 100% identity to a region of a plant gene. In another preferred embodiment, a fragment comprises a portion of a larger nucleic acid sequence. In another aspect, a fragment nucleic acid molecule has a nucleic acid sequence that has at least 15, 25, 50, or 100 contiguous nucleotides of a nucleic acid molecule of the present invention. In a preferred embodiment, a nucleic acid molecule has a nucleic acid sequence that has at least 15, 25, 50, or 100 contiguous nucleotides of a plant gene.

It is understood that a nucleic acid of the present invention can be in either orientation and that such molecules can be in a sense or antisense orientation.

A first nucleic acid segment can be physically linked to or part of a polycistronic construct with a second nucleic acid segment. Nucleic acid sequences within a first or second nucleic acid segment can be physically linked to or part of a polycistronic construct with other nucleic acid segments. A promoter can be physically linked to or part of a polycistronic construct with a first nucleic segment and second nucleic acid segment. Such polycistronic constructs can be capable of expressing a polycistronic mRNA.

i. First Nucleic Acid Segment Capable of Being Transcribed as One or More RNAs

A first nucleic acid segment can be any nucleic acid sequence that is capable of being transcribed and expressed as an mRNA. In an aspect, the nucleic acid sequence corresponds to a nucleic acid sequence that is also found in a naturally occurring gene or part of a gene such as a transcribed segment of a gene. Such a gene can be any gene from any organism. In a preferred aspect the gene is from a plant. In another preferred aspect the gene is from a microorganism. An illustrative gene is a GMT gene. A first nucleic acid segment which is transcribed and expressed as an mRNA can be translated into a protein, fragment thereof, polypeptide, or peptide. In one aspect the proteins, fragments thereof, polypeptides, or peptides are also endogenous to the host. In another aspect the proteins, fragments thereof, polypeptides, or peptides are not normally found in the plant. In a further aspect the amino acid sequence of the proteins, fragments thereof, polypeptides, or peptides are not found in a non-transformed host.

It is also understood that a first nucleic acid segment can contain sequences that encode for more than one protein, fragment thereof, polypeptide, or peptide. In this aspect, the proteins, fragments thereof, polypeptides, or peptides may be a combination of proteins, fragments thereof, polypeptides, or peptides endogenous to the host, not normally found in the plant, or not found in a non-transformed host. In this aspect, a first nucleic acid segment can encode for two, three, four, five, or more than five proteins, fragments thereof, polypeptides, or peptides.

ii. Second Nucleic Acid Sequence Capable of Suppressing One or More RNAs

A second nucleic acid segment can be any nucleic acid sequence which, when introduced into a cell or organism, is capable of effectively eliminating, substantially reducing, at least partially reducing or reducing the level of an mRNA transcript or protein encoded by a gene. In an aspect of the present invention, a gene is an endogenous gene. In an aspect of the present invention, a gene is a plant gene. An illustrative gene is a FAD2 gene.

It is also understood that a second nucleic acid segment can be any nucleic acid sequence, which, when introduced into a cell or organism, is capable of effectively eliminating, substantially reducing, at least partially reducing or reducing the level of one, two, three, four, five, or more mRNAs. It also understood in this aspect that an individual mRNA may be suppressed by different methodologies, for example RNAi and antisense suppression.

In an aspect of the invention, the second nucleic acid sequence of the present invention, which is preferably a dsRNA construct, preferably a sense RNA construct, or preferably an antisense RNA construct, is capable of providing at least a partial reduction, more preferably a substantial reduction, or most preferably effective elimination of another agent such as a protein or mRNA. In an aspect of the present invention, the other agent is a FAD2 protein or mRNA encoded by a FAD2 gene.

In another aspect, the level of one or more agents is reduced, at least partially reduced, substantially reduced or effectively eliminated while the level of one or more simultaneously, co-expressed or coordinately expressed agents is at least partially enhanced, at least enhanced, or substantially enhanced.

In a further embodiment, a nucleic acid molecule, when introduced into a cell or organism, selectively increases the level of a first protein or RNA transcript or both encoded by a first gene and at the same time reduces the level of a second protein, transcript or both encoded by a second gene, and also alters the alpha-tocopherol content, the oil composition, and the oil level of the cell or organism.

Multiple methodologies can be used to effectively eliminate, substantially reduce, or at least partially reduce the level of an mRNA transcript or protein encoded by a gene. Such methods can result in gene specific silencing or in the silencing of multiple genes. Examples of such gene silencing include, without limitation, those induced by the introduction of a double-stranded RNA molecule, antisense, and sense RNA.

In another aspect, a second nucleic acid segment can be any nucleic acid sequence which, when introduced into a cell or organism, is capable of effectively eliminating, substantially reducing, at least partially reducing or reducing the level of two, three, four, five, or more than five mRNA transcripts or proteins encoded by a gene.

a. dsRNA

Double-stranded molecules which can be used for gene silencing include dsRNA molecules that comprise nucleic acid sequences corresponding to a nucleic acid sequence found in a transcript. Such nucleic acid sequences include, without limitation, nucleic acid sequences that encode for a protein, fragment thereof, polypeptide, or peptide, and those that correspond to transcribed introns, transcribed 3' untranslated regions (UTRs), and transcribed 5' UTRs.

One subset of the second nucleic acid sequence of the nucleic acid molecules of the invention is a nucleic acid sequence which is expressed as a double-stranded RNA which comprises (1) a first RNA fragment that exhibits identity to a transcribed region of a second gene which is to be suppressed, and (2) a second RNA capable of forming a double-stranded RNA molecule with the first RNA. The first RNA fragment may consist of significant portion(s) of, or indeed most of, a plant gene which is to be suppressed.

In an aspect, a nucleic acid molecule of the present invention comprises a nucleic acid sequence which exhibits sufficient homology to one or more plant introns from a second plant gene, which when introduced into a plant cell or plant as a dsRNA construct, is capable of effectively eliminating, substantially reducing, or at least partially reducing the level of an mRNA transcript or protein encoded by the gene from which the intron(s) was derived.

In an aspect, a nucleic acid molecule of the present invention comprises a nucleic acid sequence which exhibits sufficient homology to one or more plant exons from a second plant gene, which when introduced into a plant cell or plant as a dsRNA construct, is capable of effectively eliminating, substantially reducing, or at least partially reducing the level of an mRNA transcript or protein encoded by the gene from which the exon(s) was derived.

In an aspect, a nucleic acid molecule of the present invention comprises a nucleic acid sequence which exhibits sufficient homology to one or more plant transcribed 3' UTR(s) from a second plant gene, which when introduced into a plant cell or plant as a dsRNA construct, is capable of effectively eliminating, substantially reducing, or at least partially reducing the level of an mRNA transcript or protein encoded by the gene from which the 3' UTR(s) was derived.

In an aspect, a nucleic acid molecule of the present invention comprises a nucleic acid sequence which exhibits sufficient homology to one or more plant transcribed 5' UTR(s) from a second plant gene, which when introduced into a plant cell or plant as a dsRNA construct, is capable of effectively eliminating, substantially reducing, or at least partially reducing the level of an mRNA transcript or protein encoded by the gene from which the 5' UTR(s) was derived.

In another preferred aspect, a dsRNA construct contains exon sequences, but the exon sequences do not correspond to a sufficient part of a plant exon to be capable of effectively eliminating, substantially reducing, or at least partially reducing the level of an mRNA transcript or protein encoded by a second gene from which the exon was derived. Strategies of suppressing gene expression with dsRNA constructs include that set forth in U.S. Provisional Patent Application Ser. No. 60/390,186, filed on Jun. 9, 2000.

b. Antisense Suppression

Antisense molecules which can be used for gene silencing include any molecules that comprise nucleic acid sequences corresponding to a complement of a nucleic acid sequence found in a transcript or part thereof or molecules with sufficient complementarity to act as antisense molecules. Such molecules include sequences, without limitation, that are the complement of those that encode for a protein, fragment thereof or polypeptide, and are the complement of those that correspond to transcribed introns, transcribed 3' untranslated regions (UTRs), and transcribed 5' UTRs.

Antisense approaches are a way of preventing or reducing gene function by targeting the genetic material (Mol et al., *FEBS Lett.* 268:427-430 (1990)). The objective of the antisense approach is to use a sequence complementary to the target gene to block its expression and create a mutant cell line or organism in which the level of a single chosen protein is selectively reduced or abolished. The site of inactivation and its developmental effect can be manipulated by the choice of promoter for antisense genes or by the timing of external application or microinjection. Antisense can manipulate its specificity by selecting either unique regions of the target gene or regions where it shares homology to other related genes (Hiatt et al., In: *Genetic Engineering*, Setlow (ed.), Vol. 11, New York: Plenum 49-63 (1989)).

Antisense RNA techniques involve introduction of RNA that is complementary to the target mRNA into cells, which results in specific RNA:RNA duplexes being formed by base pairing between the antisense substrate and the target mRNA (Green et al., *Annu. Rev. Biochem.* 55:569-597 (1986)). Under one embodiment, the process involves the introduction and expression of an antisense gene sequence. Such a sequence is one in which part or all of the normal gene sequences are placed under a promoter in inverted orientation so that the 'wrong' or complementary strand is transcribed into a noncoding antisense RNA that hybridizes with the target mRNA and interferes with its expression (Takayama and Inouye, *Crit. Rev. Biochem. Mol. Biol.* 25:155-184 (1990)). An antisense vector is constructed by standard procedures and introduced into cells by transformation, transfection, electroporation, microinjection, infection, etc. The type of transformation and choice of vector will determine whether expression is transient or stable. The promoter used for the antisense gene may influence the level, timing, tissue, specificity, or inducibility of the antisense inhibition.

c. Cosuppression or Sense Suppression

Sense suppression molecules which can be used for gene silencing include any molecules that comprise nucleic acid sequences corresponding to a nucleic acid sequence found in a transcript or part thereof or molecules with sufficient complementarity to act as sense molecules. Such molecules include sequences, without limitation, that encode for a protein, fragment thereof or polypeptide, and those that correspond to transcribed introns, transcribed 3' untranslated regions (UTRs), and transcribed 5' UTRs Cosuppression is the reduction in expression levels, usually at the level of RNA, of a particular endogenous gene or gene family by the expression of a homologous sense construct that is capable of transcribing mRNA of the same strandedness as the transcript of the endogenous gene (Napoli et al., *Plant Cell* 2:279-289 (1990); van der Krol et al., *Plant Cell* 2:291-299 (1990)). Cosuppression may result from stable transformation with a single copy nucleic acid molecule that is homologous to a nucleic acid sequence found within the cell (Prolls and Meyer, *Plant J.* 2:465-475 (1992)) or with multiple copies of a nucleic acid molecule that is homologous to a nucleic acid sequence found within the cell (Mittlesten et al., *Mol. Gen. Genet.* 244:325-330 (1994)). Genes, even though different, linked to homologous promoters may result in the cosuppression of the linked genes (Vaucheret, *C. R. Acad. Sci. III* 316:1471-1483 (1993); Flavell, *Proc. Natl. Acad. Sci. (U.S.A.)* 91:3490-3496 (1994); van Blokland et al., *Plant J.* 6:861-877 (1994); Jorgensen, *Trends Biotechnol.* 8:340-344 (1990); Meins and Kunz, In: *Gene Inactivation and Homologous Recombination in Plants*, Paszkowski (ed.), pp. 335-348, Kluwer Academic, Netherlands (1994)).

iii. Suppression or Expression Nucleic Acid Molecules

In one aspect of the present invention, the present invention provides a nucleic acid molecule which can encode for two, three, four, five, or more than five proteins, fragments thereof, polypeptides, or peptides operably linked to a single promoter sequence.

In another aspect of the present invention, the present invention provides a nucleic acid molecule which, when introduced into a cell or organism, is capable of effectively eliminating, substantially reducing, at least partially reducing or reducing the level of two, three, four, five, or more than five mRNA transcripts or proteins encoded by a gene, operably linked to a single promoter sequence.

C. Other Components of Construct/Vector

Constructs or vectors may also include, within the region of interest, a nucleic acid sequence that acts, in whole or in part, to terminate transcription of that region. A number of such sequences have been isolated, including the Tr7 3' sequence and the NOS 3' sequence (Ingelbrecht et al., *Plant Cell* 1:671-680 (1989); Bevan et al., *Nucleic Acids Res.* 11:369-385 (1983)). Regulatory transcript termination regions can be provided in plant expression constructs of the present invention as well. Transcript termination regions can be provided by the DNA sequence encoding the gene of interest or a convenient transcription termination region derived from a different gene source, for example, the transcript termination region that is naturally associated with the transcript initiation region. The skilled artisan will recognize that any convenient transcript termination region that is capable of terminating transcription in a plant cell can be employed in the constructs of the present invention.

A vector or construct may also include regulatory elements. Examples of such include the Adh intron 1 (Callis et al., *Genes and Develop.* 1:1183-1200 (1987)), the sucrose synthase intron (Vasil et al., *Plant Physiol.* 91:1575-1579 (1989)) and the TMV omega element (Gallie et al., *Plant Cell* 1:301-311 (1989)). These and other regulatory elements may be included when appropriate.

A vector or construct may also include a selectable marker. Selectable markers may also be used to select for plants or plant cells that contain the exogenous genetic material. Examples of such include, but are not limited to: a neo gene (Potrykus et al., *Mol. Gen. Genet.* 199:183-188 (1985)), which codes for kanamycin resistance and can be selected for using kanamycin, RptII, G418, hpt; a bar gene which codes for bialaphos resistance; a mutant EPSP synthase gene (Hinchee et al., *Bio/Technology* 6:915-922 (1988); Reynaerts et al., Selectable and Screenable Markers, In Gelvin and Schilperoort, Plant Molecular Biology Manual, Kluwer, Dordrecht (1988)); aadA (Scofield et al., *Mol. Gen. Genet.* 244 (2):189-96 (1994)), which encodes glyphosate resistance; a nitrilase gene which confers resistance to bromoxynil (Stalker et al., *J. Biol. Chem.* 263:6310-6314 (1988)); a mutant acetolactate synthase gene (ALS) which confers imidazolinone or sulphonylurea resistance (European Patent Application 154,204 (Sep. 11, 1985)); ALS (D'Halluin et al., *Bio/Technology* 10: 309-314 (1992)); and a methotrexate resistant DHFR gene (Thillet et al., *J. Biol. Chem.* 263:12500-12508 (1988)).

A vector or construct may also include a screenable marker. Screenable markers may be used to monitor expression. Exemplary screenable markers include: a β-glucuronidase or uidA gene (GUS) which encodes an enzyme for which various chromogenic substrates are known (Jefferson, *Plant Mol. Biol. Rep.* 5:387-405 (1987); Jefferson et al., *EMBO J.* 6:3901-3907 (1987)); an R-locus gene, which encodes a product that regulates the production of anthocyanin pigments (red color) in plant tissues (Dellaporta et al., *Stadler Symposium* 11:263-282 (1988)); a β-lactamase gene (Sutcliffe et al., *Proc. Natl. Acad. Sci. USA* 75:3737-3741 (1978)), a gene which encodes an enzyme for which various chromogenic substrates are known (e.g., PADAC, a chromogenic cephalosporin); a luciferase gene (Ow et al., *Science* 234:856-859 (1986)); a xylE gene (Zukowsky et al., *Proc. Natl. Acad. Sci. USA* 80:1101-1105 (1983)) which encodes a catechol dioxygenase that can convert chromogenic catechols; an α-amylase gene (Ikatu et al., *Bio/Technology* 8:241-242 (1990)); a tyrosinase gene (Katz et al., *J. Gen. Microbiol.* 129:2703-2714 (1983)) which encodes an enzyme capable of oxidizing tyrosine to DOPA and dopaquinone which in turn condenses to melanin; and an α-galactosidase gene, which encodes an enzyme which will turn a chromogenic α-galactose substrate.

Included within the terms "selectable or screenable marker genes" are also genes that encode a secretable marker whose secretion can be detected as a means of identifying or selecting for transformed cells. Examples include markers that encode a secretable antigen that can be identified by antibody interaction, or even secretable enzymes that can be detected catalytically. Secretable proteins fall into a number of classes, including small, diffusible proteins that are detectable, (e.g., by ELISA), small active enzymes that are detectable in extracellular solution (e.g., α-amylase, β-lactamase, phosphinothricin transferase), or proteins that are inserted or trapped in the cell wall (such as proteins that include a leader sequence such as that found in the expression unit of extension or tobacco PR-S). Other possible selectable and/or screenable marker genes will be apparent to those of skill in the art.

Transgenic Plants, Parts Thereof and Plant Cells

Exogenous genetic material may be transferred into a plant cell and the plant cell can be regenerated into a whole, fertile or sterile plant or plant part. Exogenous genetic material is any genetic material, whether naturally occurring or otherwise, from any source that is capable of being inserted into any organism. Such exogenous genetic material includes, without limitation, nucleic acid molecules and constructs that comprise a nucleic acid sequence of the present invention, as set forth within.

In a preferred aspect, a plant cell or plant of the present invention includes a nucleic acid molecule comprising a first and second nucleic acid sequence, where the first nucleic acid sequence which, when it is expressed, is capable of at least partially enhancing, increasing, enhancing, or substantially enhancing the level of an mRNA transcript or protein and where the second nucleic acid sequence exhibits sufficient homology to one or more plant genes such that when it is expressed, it is capable of effectively eliminating, substantially reducing, or at least partially reducing the level of an mRNA transcript or protein encoded by the gene from which it was derived or any gene which has homology to that gene.

It is understood that any methodology that will suppress the expression of a gene can be used.

In an aspect of the present invention, a plant cell or plant of the present invention includes a nucleic acid molecule that comprises a nucleic acid sequence which is capable of increasing the protein, transcript or both encoded by a GMT gene and at the same time selectively reducing the protein, transcript or both encoded by a FAD2 gene.

In a preferred aspect, a plant cell or plant of the present invention includes a nucleic acid molecule that comprises a first nucleic acid segment and a second nucleic acid segment, where the first nucleic acid segment, the second nucleic acid segment, or both, are capable of altering seed oil composition. In a more preferred aspect, the first nucleic acid sequence, when it is expressed, is capable of increasing the level of alpha-tocopherol, and the second nucleic acid segment exhibits sufficient homology to complements of one or more plant genes such that when it is expressed, it is capable of increasing the level of oleic acid or oil content, or both, the first nucleic acid sequence and the second nucleic acid sequence being operably linked to a single promoter sequence.

Genetic material may be introduced into any species, for example, without limitation monocotyledons or dicotyledons, including, but not limited to alfalfa, apple, *Arabidopsis*, banana, barley, *Brassica campestris*, canola, castor bean, chrysanthemum, coffee, cotton, cottonseed, corn, crambe, cranberry, cucumber, dendrobium, dioscorea, eucalyptus, fescue, flax, gladiolus, liliacea, linseed, millet, muskmelon, mustard, oat, oil palm, oilseed rape, papaya, peanut, perennial, *Phaseolus*, potato, rapeseed, rice, rye, ryegrass, safflower, sesame, sorghum, soybean, sugarbeet, sugarcane, sunflower, tobacco, tomato, turfgrass, and wheat (Christou, I N O: *Particle Bombardment for Genetic Engineering of Plants*, Biotechnology Intelligence Unit. Academic Press, San Diego, Calif. (1996)), with alfalfa, *Arabidopsis, Brassica campestris*, canola, castor bean, corn, cotton, cottonseed, crambe, flax, linseed, mustard, oil palm, oilseed rape, peanut, potato, rapeseed, safflower, sesame, soybean, sunflower, tobacco, tomato, and wheat preferred, and *Brassica campestris*, canola, corn, oil palm, oilseed rape, peanut, rapeseed, safflower, soybean, and sunflower more preferred. In a more preferred aspect, genetic material is transferred into canola. In another more preferred aspect, genetic material is transferred into oilseed rape. In another particularly preferred embodiment, genetic material is transferred into soybean or corn.

Genetic material may also be introduced into a suitable cell such as a plant cell. The cell may be present in a multi-cellular environment. In an aspect of the present invention, the multicellular environment may be in a transformed plant.

Genetic material may also be introduced into a cell or organism such as a mammalian cell, mammal, fish cell, fish, bird cell, bird, algae cell, algae, fungal cell, fungi, or bacterial cell. Preferred host and transformants include: fungal cells such as *Aspergillus*, yeasts, mammals, particularly bovine and porcine, insects, bacteria, and algae. Particularly preferred bacteria are *Agrobacterium tumefaciens* and *E. coli*.

The levels of products such as transcripts or proteins may be increased or decreased or both throughout an organism such as a plant or localized in one or more specific organs or tissues of the organism. For example the levels of products may be increased or decreased in one or more of the tissues and organs of a plant including without limitation: roots, tubers, stems, leaves, stalks, fruit, berries, nuts, bark, pods, seeds and flowers. A preferred organ is a seed.

In an aspect of the invention, after transformation of a plant or other organism with a nucleic acid of the present invention, the level of one or more agents is at least partially enhanced, increased, enhanced, or substantially enhanced, while a second agent is simultaneously expressed, coexpressed, or coordinately expressed with the first agent.

In another aspect, after transformation of a plant or other organism with a nucleic acid of the present invention, the level of one or more agents is at least partially enhanced, increased, enhanced, or substantially enhanced, while a second agent is simultaneously expressed, coexpressed, or coordinately expressed, and the simultaneous expression, coexpression or coordinate expression of the second agent results in a reduction, preferably at least a partial reduction, substantial reduction or effective elimination of another agent.

In another aspect, after transformation of a plant or other organism with a nucleic acid of the present invention, the level of one or more agents is at least partially enhanced, increased, enhanced, or substantially enhanced, while a second agent is simultaneously expressed, coexpressed, or coordinately expressed with two or greater than two agents.

In another aspect, after transformation of a plant or other organism with a nucleic acid of the present invention, the level of one or more agents is at least partially enhanced, increased, enhanced, or substantially enhanced, while a second agent is simultaneously expressed, coexpressed, or coordinately expressed with three or greater than three agents.

In another aspect, after transformation of a plant or other organism with a nucleic acid of the present invention, the level of one or more agents is at least partially enhanced, increased, or substantially enhanced while additional agents are simultaneously expressed, coexpressed or coordinately expressed with the first agent and the simultaneous expression, coexpression or coordinated expression of the additional agents, preferably two or more, three or more, four or more, or five or more agents, result in at least partial reduction, substantial reduction or an effective elimination of more than one agent, preferably two or more, three or more, four or more, or five or more agents.

In an aspect, after transformation of a plant or other organism with a nucleic acid of the present invention, one or more agents is at least partially enhanced, increased, enhanced, or substantially enhanced while another agent or agents is simultaneously expressed, coexpressed, or coordinately expressed and such expression results in at least a partial reduction, a substantial reduction, or effective elimination of an agent or agents.

When levels of an agent are compared, such a comparison is preferably carried out between organisms with a similar genetic background. In a preferred aspect, a similar genetic background is a background where the organisms being compared share 50% or greater of their nuclear genetic material. In a more preferred aspect a similar genetic background is a background where the organisms being compared share 75% or greater, even more preferably 90% or greater of their nuclear genetic material. In another even more preferable aspect, a similar genetic background is a background where the organisms being compared are plants, and the plants are isogenic except for any genetic material originally introduced using plant transformation techniques.

In a preferred aspect, the capability of a nucleic acid sequence to partially enhance, enhance or substantially enhance the level of an agent is carried out by a comparison of levels of mRNA transcripts. In a preferred aspect, the capability of a nucleic acid sequence to partially enhance, enhance, or substantially enhance the level of a gene relative to another gene is carried out by a comparison of levels of proteins, fragments thereof or polypeptides encoded by the genes. In a preferred aspect, the capability of a nucleic acid sequence to reduce the level of a gene relative to another gene is carried out by a comparison of levels of mRNA transcripts. In a preferred aspect, the capability of a nucleic acid sequence to reduce the level of a gene relative to another gene is carried out by a comparison of levels of proteins, fragments thereof or polypeptides encoded by the genes. As used herein, mRNA transcripts include processed and non-processed mRNA transcripts. As used herein, proteins, fragments thereof or polypeptides include proteins, fragments thereof or polypeptides with or without any post-translational modification. In another preferred aspect, the capability of a nucleic acid molecule to increase the level of a gene relative to another gene is carried out by a comparison of phenotype. In a preferred aspect, the comparison of phenotype is a comparison of alpha-tocopherol content. In a preferred aspect, the comparison of phenotype is a comparison of fatty acid composition. In a preferred aspect, the comparison of phenotype is a comparison of total oil level.

Methods of Introducing Nucleic Acid Molecules into Plants or Organisms

There are many methods for introducing nucleic acid molecules into plant cells. Suitable methods are believed to include virtually any method by which nucleic acid molecules may be introduced into a cell, such as by *Agrobacterium* infection or direct delivery of nucleic acid molecules such as, for example, by transfection, injection, projection, PEG-mediated transformation, by electroporation or by acceleration of DNA coated particles, and the like. (Potrykus, *Ann. Rev. Plant Physiol. Plant Mol. Biol.* 42:205-225 (1991); Vasil, *Plant Mol. Biol.* 25:925-937 (1994)). For example, electroporation has been used to transform corn protoplasts (Fromm et al., *Nature* 312:791-793 (1986)).

Nucleic acids can also be introduced into an organism via methods including, but not limited to, conjugation, endocytosis, and phagocytosis. Furthermore, the nucleic acid can be introduced into a cell or organism derived from a plant, plant cell, algae, algae cell, fungus, fungal cell, bacterial cell, mammalian cell, fish cell, or bird cell. Particularly preferred microorganisms are *E. coli* and *Agrobacterium* species.

Technology for introduction of DNA into cells is well known to those of skill in the art. Four general methods for delivering a gene into cells have been described: (1) chemical methods (Graham and van der Eb, *Virology* 54:536-539 (1973)); (2) physical methods such as microinjection (Capecchi, *Cell* 22:479-488 (1980)), electroporation (Wong and Neumann, *Biochem. Biophys. Res. Commun.* 107:584-587 (1982); Fromm et al., *Proc. Natl. Acad. Sci. USA* 82:5824-5828 (1985); U.S. Pat. No. 5,384,253); the gene gun (Johnston and Tang, *Methods Cell Biol.* 43:353-365 (1994)); and vacuum infiltration (Bechtold et al., *C. R. Acad. Sci. Paris, Life Sci.* 316:1194-1199. (1993)); (3) viral vectors (Clapp, *Clin. Perinatol.* 20:155-168 (1993); Lu et al., *J. Exp. Med.* 178:2089-2096 (1993); Eglitis and Anderson, *Biotechniques* 6:608-614 (1988)); and (4) receptor-mediated mechanisms (Curiel et al., *Hum. Gen. Ther.* 3:147-154 (1992); Wagner et al., *Proc. Natl. Acad. Sci. USA* 89:6099-6103 (1992)).

Acceleration methods that may be used include, for example, microprojectile bombardment and the like. One example of a method for delivering transforming nucleic acid molecules into plant cells is microprojectile bombardment. This method has been reviewed by Yang and Christou (eds.), *Particle Bombardment Technology for Gene Transfer*, Oxford Press, Oxford, England (1994). Non-biological particles (microprojectiles) may be coated with nucleic acid molecules and delivered into cells by a propelling force. Exemplary particles include those comprised of tungsten, gold, platinum and the like.

A particular advantage of microprojectile bombardment, in addition to it being an effective way of reproducibly transforming monocots, is that neither the isolation of protoplasts (Cristou et al., *Plant Physiol.* 87:671-674 (1988)) nor the susceptibility to *Agrobacterium* infection is required. An illustrative embodiment of a method for delivering DNA into corn cells by acceleration is a biolistics α-particle delivery system, which can be used to propel particles coated with DNA through a screen, such as a stainless steel or Nytex screen, onto a filter surface covered with corn cells cultured in suspension. Gordon-Kamm et al., describes the basic procedure for coating tungsten particles with DNA (Gordon-Kamm et al., *Plant Cell* 2:603-618 (1990)). The screen disperses the tungsten nucleic acid particles so that they are not delivered to the recipient cells in large aggregates. A particle delivery system suitable for use with the invention is the helium acceleration PDS-1000/He gun, which is available from Bio-Rad Laboratories (Bio-Rad, Hercules, Calif.) (Sanford et al., *Technique* 3:3-16 (1991)).

For the bombardment, cells in suspension may be concentrated on filters. Filters containing the cells to be bombarded are positioned at an appropriate distance below the microprojectile stopping plate. If desired, one or more screens are also positioned between the gun and the cells to be bombarded.

Alternatively, immature embryos or other target cells may be arranged on solid culture medium. The cells to be bombarded are positioned at an appropriate distance below the microprojectile stopping plate. If desired, one or more screens are also positioned between the acceleration device and the cells to be bombarded. Through the use of techniques set forth herein one may obtain 1000 or more loci of cells transiently expressing a marker gene. The number of cells in a focus that express the exogenous gene product 48 hours post-bombardment often ranges from one to ten, and average one to three.

In bombardment transformation, one may optimize the pre-bombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment and also the nature of the transforming DNA, such as linearized DNA or intact supercoiled plasmids. It is believed that pre-bombardment manipulations are especially important for successful transformation of immature embryos.

Accordingly, it is contemplated that one may wish to adjust various aspects of the bombardment parameters in small-scale studies to fully optimize the conditions. One may particularly wish to adjust physical parameters such as gap distance, flight distance, tissue distance and helium pressure. One may also minimize the trauma reduction factors by modifying conditions that influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example the methods described by Fraley et al., *Bio/Technology* 3:629-635 (1985) and Rogers et al., *Methods Enzymol.* 153:253-277 (1987). Further, the integration of the Ti-DNA is a relatively precise process resulting in few rearrangements. The region of DNA to be transferred is defined by the border sequences and intervening DNA is usually inserted into the plant genome as described (Spielmann et al., *Mol. Gen. Genet.* 205:34 (1986)).

Modern *Agrobacterium* transformation vectors are capable of replication in *E. coli* as well as *Agrobacterium*, allowing for convenient manipulations as described in Klee et al., in *Plant DNA Infectious Agents*, Hohn and Schell (eds.), Springer-Verlag, New York, pp. 179-203 (1985). Moreover, technological advances in vectors for *Agrobacterium*-mediated gene transfer have improved the arrangement of genes and restriction sites in the vectors to facilitate construction of vectors capable of expressing various polypeptide-coding genes. The vectors described have convenient multi-linker regions flanked by a promoter and a polyadenylation site for direct expression of inserted polypeptide coding genes and are suitable for present purposes (Rogers et al., *Methods Enzymol.* 153:253-277 (1987)). In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

A transgenic plant formed using *Agrobacterium* transformation methods typically contains a single gene on one chromosome. Such transgenic plants can be referred to as being heterozygous for the added gene. More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant, a transgenic plant that contains a single added gene, germinating some of the seed produced and analyzing the resulting plants produced for the gene of interest.

It is also to be understood that two different transgenic plants can also be mated to produce offspring that contain two independently segregating, exogenous constructs. Selfing of appropriate progeny can produce plants that are homozygous for both added, exogenous genes that encode a polypeptide of interest. Backcrossing to a parental plant and out-crossing with a non-transgenic plant are also contemplated, as is vegetative propagation.

Transformation of plant protoplasts can be achieved using methods based on calcium phosphate precipitation, polyethylene glycol treatment, electroporation and combinations of these treatments (See, e.g., Potrykus et al., *Mol. Gen. Genet.* 205:193-200 (1986); Lorz et al., *Mol. Gen. Genet.* 199:178 (1985); Fromm et al., *Nature* 319:791 (1986); Uchimiya et al., *Mol. Gen. Genet.* 204:204 (1986); Marcotte et al., *Nature* 335:454-457 (1988)). Application of these systems to different plant strains depends upon the ability to regenerate that particular plant strain from protoplasts. Illustrative methods for the regeneration of cereals from protoplasts are described (Fujimura et al., *Plant Tissue Culture Letters* 2:74 (1985); Toriyama et al., *Theor. Appl. Genet.* 205:34 (1986); Yamada et al., *Plant Cell Rep.* 4:85 (1986); Abdullah et al., *Biotechnology* 4:1087 (1986)).

To transform plant strains that cannot be successfully regenerated from protoplasts, other ways to introduce DNA into intact cells or tissues can be utilized. For example, regeneration of cereals from immature embryos or explants can be effected as described (Vasil, *Bio/Technology* 6:397 (1988)). In addition, "particle gun" or high-velocity microprojectile technology can be utilized (Vasil et al., *Bio/Technology* 10:667 (1992)). Using the latter technology, DNA is carried through the cell wall and into the cytoplasm on the surface of small metal particles as described (Klein et al., *Nature* 328:70 (1987); Klein et al., *Proc. Natl. Acad. Sci. USA* 85:8502-8505 (1988); McCabe et al., *Bio/Technology* 6:923 (1988)). The metal particles penetrate through several layers of cells and thus allow the transformation of cells within tissue explants.

Methods for transforming dicots, primarily by use of *Agrobacterium tumefaciens* and obtaining transgenic plants have been published for cotton (U.S. Pat. No. 5,004,863; U.S. Pat. No. 5,159,135; U.S. Pat. No. 5,518,908); soybean (U.S. Pat. No. 5,569,834; U.S. Pat. No. 5,416,011; McCabe et al., *Biotechnology* 6:923 (1988); Christou et al., *Plant Physiol.* 87:671-674 (1988)); Brassica (U.S. Pat. No. 5,463,174); peanut (Cheng et al., *Plant Cell Rep.* 15:653-657 (1996), McKently et al., *Plant Cell Rep.* 14:699-703 (1995)); papaya; pea (Grant et al., *Plant Cell Rep.* 15:254-258 (1995)); and *Arabidopsis thaliana* (Bechtold et al., *C. R. Acad. Sci. Paris, Life Sci.* 316:1194-1199 (1993)). The latter method for transforming *Arabidopsis thaliana* is commonly called "dipping" or vacuum infiltration or germplasm transformation.

Transformation of monocotyledons using electroporation, particle bombardment and *Agrobacterium* have also been reported. Transformation and plant regeneration have been achieved in asparagus (Bytebier et al., *Proc. Natl. Acad. Sci. (USA)* 84:5354 (1987)); barley (Wan and Lemaux, *Plant Physiol* 104:37 (1994)); corn (Rhodes et al., *Science* 240:204

(1988); Gordon-Kamm et al., *Plant Cell* 2:603-618 (1990); Fromm et al., *Bio/Technology* 8:833 (1990); Koziel et al., *Bio/Technology* 11:194 (1993); Armstrong et al., *Crop Science* 35:550-557 (1995)); oat (Somers et al., *Bio/Technology* 10:1589 (1992)); orchard grass (Horn et al., *Plant Cell Rep.* 7:469 (1988)); rice (Toriyama et al., *Theor Appl. Genet.* 205: 34 (1986); Part et al., *Plant Mol. Biol.* 32:1135-1148 (1996); Abedinia et al., *Aust. J. Plant Physiol.* 24:133-141 (1997); Zhang and Wu, *Theor. Appl. Genet.* 76:835 (1988); Zhang et al., *Plant Cell Rep.* 7:379 (1988); Battraw and Hall, *Plant Sci.* 86:191-202 (1992); Christou et al., *Bio/Technology* 9:957 (1991)); rye (De la Pena et al., *Nature* 325:274 (1987)); sugarcane (Bower and Birch, *Plant J.* 2:409 (1992)); tall fescue (Wang et al., *Bio/Technology* 10:691 (1992)) and wheat (Vasil et al., *Bio/Technology* 10:667 (1992); U.S. Pat. No. 5,631,152).

Assays for gene expression based on the transient expression of cloned nucleic acid constructs have been developed by introducing the nucleic acid molecules into plant cells by polyethylene glycol (PEG) treatment, electroporation, or particle bombardment (Marcotte et al., *Nature* 335:454-457 (1988); Marcotte et al., *Plant Cell* 1:523-532 (1989); McCarty et al., *Cell* 66:895-905 (1991); Hattori et al., *Genes Dev.* 6:609-618 (1992); Goff et al., *EMBO J.* 9:2517-2522 (1990)). Transient expression systems may be used to functionally dissect gene constructs (see generally, Maliga et al., *Methods in Plant Molecular Biology*, Cold Spring Harbor Press (1995)).

Any of the nucleic acid molecules of the invention may be introduced into a plant cell in a permanent or transient manner. A nucleic acid molecule of the present invention may be stably integrated into a nuclear, chloroplast or mitochondrial genome, preferably into the nuclear genome.

Other methods of cell or organism transformation can also be used and include but are not limited to introduction of DNA into plants by direct DNA transfer into pollen (Hess et al., *Intern Rev. Cytol.* 107:367 (1987); Luo et al., *Plant Mol Biol. Reporter* 6:165 (1988)), by direct injection of DNA into reproductive organs of a plant (Pena et al., *Nature* 325:274 (1987)), by direct microinjection of DNA into protoplasts (Crossway et al., *Mol. Gen. Genet.* 202: 179-185 (1986)), or by direct injection of DNA into the cells of immature embryos followed by the rehydration of desiccated embryos (Neuhaus et al., *Theor. Appl. Genet.* 75:30 (1987)). See also EP 0 238 023; Yelton et al., *Proc. Natl. Acad. Sci. (U.S.A.)*, 81:1470-1474 (1984); Malardier et al., *Gene*, 78:147-156 (1989); Becker and Guarente, In: Abelson and Simon (eds.), *Guide to Yeast Genetics and Molecular Biology, Method Enzymol.*, Vol. 194, pp. 182-187, Academic Press, Inc., New York; Ito et al., *J. Bacteriology*, 153:163 (1983); Hinnen et al., *Proc. Natl. Acad. Sci. (U.S.A.)*, 75:1920 (1978); and Bennett and LaSure (eds.), *More Gene Manipualtionins in fungi*, Academic Press, CA (1991).

The regeneration, development and cultivation of plants from single plant protoplast transformants or from various transformed explants are well known in the art (Weissbach and Weissbach, *In Methods for Plant Molecular Biology*, Academic Press, San Diego, Calif., (1988)). This regeneration and growth process typically includes the steps of selection of transformed cells and culturing those individualized cells through the usual stages of embryonic development and through the rooted plantlet stage. Transgenic embryos and seeds are similarly regenerated. The resulting transgenic rooted shoots are thereafter planted in an appropriate plant growth medium such as soil.

The development or regeneration of plants containing a foreign, exogenous gene that encodes a protein of interest is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the invention containing a desired polypeptide is cultivated using methods well known to one skilled in the art.

There are a variety of methods for the regeneration of plants from plant tissue. The particular method of regeneration will depend on the starting plant tissue and the particular plant species to be regenerated.

The present invention also provides for the generation of parts of the plants, particularly reproductive or storage parts. Plant parts, without limitation, include seeds, endosperm, ovule, pollen, roots, tubers, stems, leaves, stalks, fruit, berries, nuts, bark, pods, and flowers. In a particularly preferred embodiment of the present invention, the plant part is a seed.

Any of the plants or parts thereof of the present invention may be processed to produce a feed, meal, protein, or oil preparation. A particularly preferred plant part for this purpose is a seed. In a preferred embodiment, the feed, meal, protein or oil preparation is designed for livestock animals or humans, or both. Methods to produce feed, meal, protein and oil preparations are known in the art. See, for example, U.S. Pat. Nos. 4,957,748, 5,100,679, 5,219,596, 5,936,069, 6,005,076, 6,146,669, and 6,156,227. In a preferred embodiment, the protein preparation is a high protein preparation. Such a high protein preparation preferably has a protein content of greater than 5% w/v, more preferably 10% w/v, and even more preferably 15% w/v. In a preferred oil preparation, the oil preparation is a high oil preparation with an oil content derived from a plant or part thereof of the present invention of greater than 5% w/v, more preferably 10% w/v, and even more preferably 15% w/v. In a preferred embodiment, the oil preparation is a liquid. In a preferred embodiment, the oil preparation is of a volume greater than 1, 5, 10 or 50 liters. The present invention provides for oil produced from plants of the present invention or generated by a method of the present invention. Such oil may exhibit enhanced oxidative stability. Also, such oil may be a minor or major component of any resultant product. Moreover, such oil may be blended with other oils. In a preferred embodiment, the oil produced from plants of the present invention or generated by a method of the present invention constitutes greater than 0.5%, 1%, 5%, 10%, 25%, 50%, 75% or 90% by volume or weight of the oil component of any composition. In another embodiment, the oil preparation may be blended and can constitute greater than 10%, 25%, 35%, 50% or 75% of the blend by volume. Oil produced from a plant of the present invention can be admixed with one or more organic solvents or petroleum distillates.

Plants of the present invention can be part of or generated from a breeding program. The choice of breeding method depends on the mode of plant reproduction, the heritability of the trait(s) being improved, and the type of cultivar used commercially (e.g., $F_1$ hybrid cultivar, pureline cultivar, etc). Selected, non-limiting approaches, for breeding the plants of the present invention are set forth below. A breeding program can be enhanced using marker-assisted selection of the progeny of any cross. It is further understood that any commercial and non-commercial cultivars can be utilized in a breeding program. Factors such as, for example, emergence vigor, vegetative vigor, stress tolerance, disease resistance, branching, flowering, seed set, seed size, seed density, standability, and threshability will generally dictate the choice.

For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection. In a preferred embodiment, a backcross or recurrent breeding program is undertaken.

The complexity of inheritance influences choice of the breeding method. Backcross breeding can be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Breeding lines can be tested and compared to appropriate standards in environments representative of the commercial target area(s) for two or more generations. The best lines are candidates for new commercial cultivars; those still deficient in traits may be used as parents to produce new populations for further selection.

One method of identifying a superior plant is to observe its performance relative to other experimental plants and to a widely grown standard cultivar. If a single observation is inconclusive, replicated observations can provide a better estimate of its genetic worth. A breeder can select and cross two or more parental lines, followed by repeated selfing and selection, producing many new genetic combinations.

The development of new cultivars requires the development and selection of varieties, the crossing of these varieties and the selection of superior hybrid crosses. The hybrid seed can be produced by manual crosses between selected male-fertile parents or by using male sterility systems. Hybrids are selected for certain single gene traits such as pod color, flower color, seed yield, pubescence color, or herbicide resistance, which indicate that the seed is truly a hybrid. Additional data on parental lines, as well as the phenotype of the hybrid, influence the breeder's decision whether to continue with the specific hybrid cross.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes. New cultivars can be evaluated to determine which have commercial potential.

Pedigree breeding is used commonly for the improvement of self-pollinating crops. Two parents who possess favorable, complementary traits are crossed to produce an $F_1$. A $F_2$ population is produced by selfing one or several $F_1$'s. Selection of the best individuals from the best families is carried out. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Backcross breeding has been used to transfer genes for a simply inherited, highly heritable trait into a desirable homozygous cultivar or inbred line, which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting parent is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seed of a population each generation of inbreeding.

Descriptions of other breeding methods that are commonly used for different traits and crops can be found in one of several reference books (e.g. Fehr, *Principles of Cultivar Development* Vol. 1, pp. 2-3 (1987)).

A transgenic plant of the present invention may also be reproduced using apomixis. Apomixis is a genetically controlled method of reproduction in plants where the embryo is formed without union of an egg and a sperm. There are three basic types of apomictic reproduction: 1) apospory where the embryo develops from a chromosomally unreduced egg in an embryo sac derived from the nucleus, 2) diplospory where the embryo develops from an unreduced egg in an embryo sac derived from the megaspore mother cell, and 3) adventitious embryony where the embryo develops directly from a somatic cell. In most forms of apomixis, pseudogamy or fertilization of the polar nuclei to produce endosperm is necessary for seed viability. In apospory, a nurse cultivar can be used as a pollen source for endosperm formation in seeds. The nurse cultivar does not affect the genetics of the aposporous apomictic cultivar since the unreduced egg of the cultivar develops parthenogenetically, but makes possible endosperm production. Apomixis is economically important, especially in transgenic plants, because it causes any genotype, no matter how heterozygous, to breed true. Thus, with apomictic reproduction, heterozygous transgenic plants can maintain their genetic fidelity throughout repeated life cycles. Methods for the production of apomictic plants are known in the art. See, e.g., U.S. Pat. No. 5,811,636.

The following examples are illustrative and not intended to be limiting in any way.

Example 1

This example illustrates constructs which were prepared to demonstrate the practice of this invention.

With reference to FIG. 1 there is shown schematically the elements of a DNA construct comprising in series (a) DNA of a napin promoter,
(b) DNA coding for gamma methyl transferenase (GMT) isolated from *Gossypium hirsutium* (cotton),
(c) sense oriented DNA of the 3' UTR of *Arabidopsis thaliana* fad2,
(d) DNA of an intron in the *Arabidopsis thaliana* fad2 with splice sites removed, (e) the complement of the (c) element, i.e. the antisense oriented DNA of the 3'UTR of *Arabidopsis thaliana* fad2, and (f) DNA of a napin 3' terminator.

The construct was inserted together with a BAR marker element into a vector between TI borders from *Agrobacterium tumefaciens*. With reference to SEQ ID NO: 5 the pertinent DNA elements of a vector, which was designated pMON75565, are described in Table 1.

TABLE 1

Elements of vector pMON75565

| Bases | description of DNA segment |
|---|---|
| 1-285 | *Agrobacterium tumefaciens* right border |
| 520-2282 | napin promoter |
| 2344-3381 | *Gossypium hirsutium* gmt |
| 3425-3470 | napin 3' transcription terminator |
| 3545-3678 | fad2 3' UTR in sense orientation |
| 3687-4818 | fad2 intron |
| 4823-4947 | fad2 3' UTR in antisense orientation |
| 4985-6199 | napin 3' transcription terminator |
| 6381-6780 | CaMV 35S promoter |
| 6781-7328 | BAR marker gene |
| 7333-7590 | NOS transcription terminator |
| 7597-8179 | *Agrobacterium tumefaciens* left border |

Figure 2:
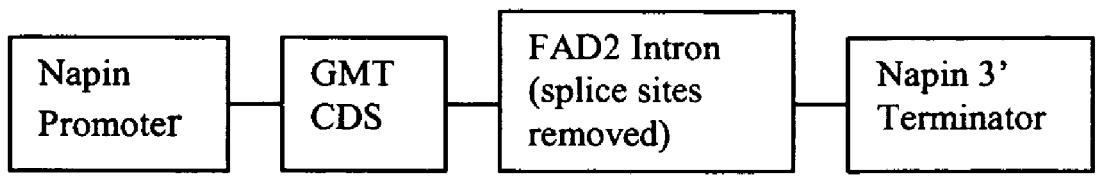
FIG. 2 is a schematic of DNA construct elements in vector pMON75571.

With reference to FIG. 2 there is shown schematically the elements of a DNA construct comprising in series (a) DNA of a napin promoter, (b) DNA coding for gamma methyl transferenase (GMT) isolated from *Gossypium hirsutium* (cotton), (c) DNA of an intron in the *Arabidopsis thaliana* fad2 with splice sites removed, and (d) DNA of a napin 3' terminator.

The construct was inserted together with a BAR marker element into a vector between TI borders from *Agrobacterium tumefaciens*. With reference to SEQ ID NO: 6 the pertinent DNA elements of a vector, which was designated pMON75571, are described in Table 2.

TABLE 2

Elements of vector pMON75571

| Bases | description of DNA segment |
|---|---|
| 1-285 | *Agrobacterium tumefaciens* right border |
| 520-2282 | napin promoter |
| 2344-3381 | *Gossypium hirsutium* gmt |
| 3396-4515 | fad2 intron |
| 4519-5733 | napin 3' transcription terminator |
| 5915-6314 | CaMV 35S promoter |
| 6315-6862 | BAR marker gene |
| 6867-7124 | NOS transcription terminator |
| 7131-7713 | *Agrobacterium tumefaciens* left border |

Transformation of Plants with pMON75565 and pMON75571

Vectors, pMON75565 and pMON75571, are used in *Arabidopsis thaliana* plant transformation to direct the expression of GMT and inhibit the expression of the fad2 gene. Binary vector constructs pMON75565 and pMON75571 are transformed into ABI strain *Agrobacterium* cells by the method of Holsters et al., *Mol. Gen. Genet.* 163:181-187 (1978). Transgenic *Arabidopsis thaliana* plants are obtained by *Agrobacterium*-mediated transformation as described by Valverkens et al., *Proc. Nat. Acad. Sci. USA* 85:5536-5540 (1988), Bent et al., *Science* 265:1856-1860 (1994), and Bechtold et al., *C. R. Acad. Sci., Life Sciences* 316:1194-1199 (1993). Transgenic plants are selected by sprinkling the transformed $R_1$ seeds directly onto soil and then vernalizing them at 4° C. in the absence of light for 4 days. The seeds are then transferred to 21° C., 16 hours light and sprayed with a 1:200 dilution of Finale (Basta) herbicide at 7 days and 14 days after seeding. Transformed plants are grown to maturity and the $R_2$ seed that is produced is analyzed for tocopherol content.

Figure 3A:
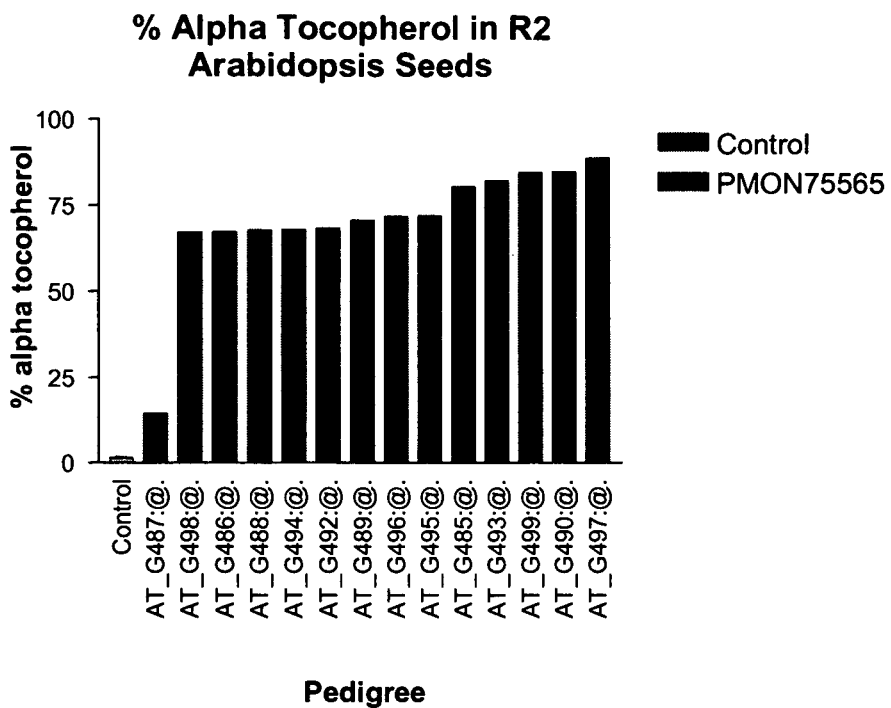
FIGS. 3A and 3B are graphs depicting the percentage of alpha-tocopherol in the total tocopherol content of *Arabidopsis* seeds from the $R_2$ generation of plants transformed with pMON75565 or pMON75571, respectively.
Figure 3B:
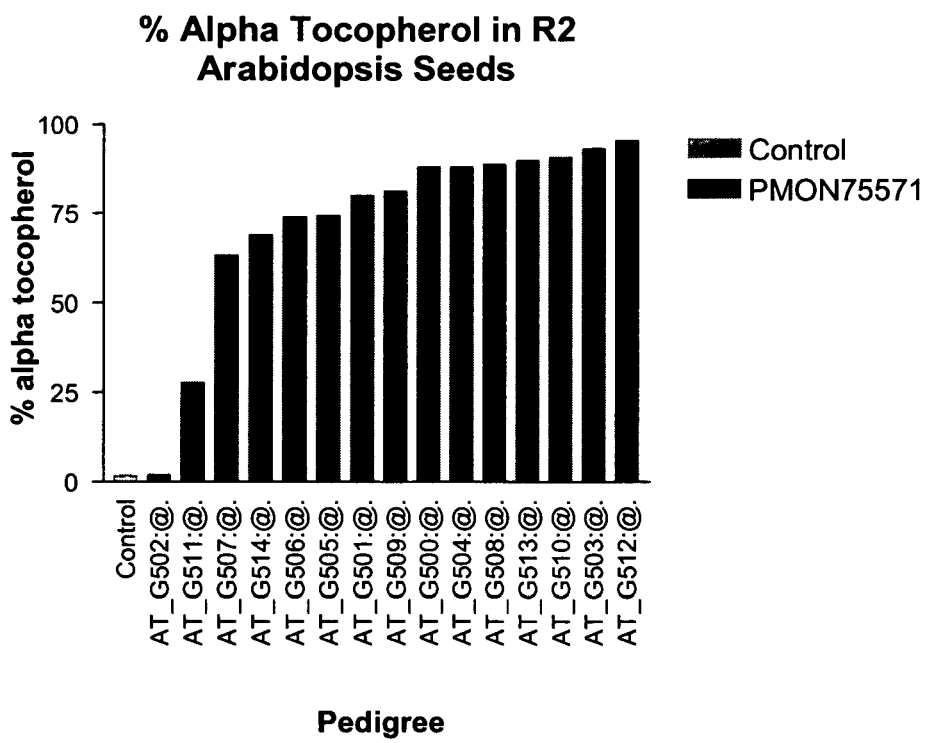

FIGS. 3A and 3B show data from the alpha-tocopherol level analysis from $R_2$ seed of transgenic *Arabidopsis thaliana* plants expressing GMTs from pMON75565 (top) or pMON75571 (bottom) under the control of the napin seed-specific promoter. Table 3 below gives specific tocopherol level results (alpha, gamma and delta) for various transformed and control plant lines.

TABLE 3

| Construct | alpha Toco | gamma Toco | delta Toco | total Toco | % alpha | Generation |
|---|---|---|---|---|---|---|
| Control | 7 | 453 | 12 | 472 | 1.5 | R3 |
| | 9 | 446 | 12 | 467 | 1.9 | R3 |
| | 5 | 440 | 10 | 455 | 1.1 | R3 |
| | 7 | 460 | 12 | 479 | 1.5 | R3 |
| | 9 | 460 | 13 | 482 | 1.9 | R3 |
| | 6 | 443 | 10 | 459 | 1.3 | R3 |
| | 6 | 459 | 11 | 476 | 1.3 | R3 |
| | 8 | 456 | 10 | 474 | 1.7 | R3 |
| | 6 | 447 | 11 | 464 | 1.3 | R3 |
| | 7 | 436 | 9 | 452 | 1.5 | R3 |
| pMON 75565 | 67 | 386 | 11 | 464 | 14.4 | R2 |
| | 320 | 152 | 5 | 477 | 67.1 | R2 |
| | 304 | 142 | 6 | 452 | 67.3 | R2 |
| | 309 | 142 | 5 | 456 | 67.8 | R2 |
| | 292 | 134 | 4 | 430 | 67.9 | R2 |
| | 320 | 143 | 5 | 468 | 68.4 | R2 |
| | 360 | 145 | 5 | 510 | 70.6 | R2 |
| | 317 | 121 | 4 | 442 | 71.7 | R2 |
| | 329 | 124 | 4 | 457 | 72.0 | R2 |
| | 336 | 79 | 3 | 418 | 80.4 | R2 |
| | 369 | 78 | 3 | 450 | 82.0 | R2 |
| | 392 | 68 | 4 | 464 | 84.5 | R2 |
| | 391 | 66 | 4 | 461 | 84.8 | R2 |
| | 422 | 51 | 2 | 475 | 88.8 | R2 |
| pMON 75571 | 10 | 492 | 13 | 515 | 1.9 | R2 |
| | 137 | 350 | 8 | 495 | 27.7 | R2 |
| | 296 | 166 | 5 | 467 | 63.4 | R2 |
| | 313 | 136 | 5 | 454 | 68.9 | R2 |
| | 364 | 124 | 4 | 492 | 74.0 | R2 |
| | 354 | 119 | 3 | 476 | 74.4 | R2 |
| | 371 | 91 | 2 | 464 | 80.0 | R2 |
| | 381 | 87 | 2 | 470 | 81.1 | R2 |
| | 391 | 52 | 2 | 445 | 87.9 | R2 |
| | 422 | 55 | 3 | 480 | 87.9 | R2 |
| | 436 | 54 | 2 | 492 | 88.6 | R2 |
| | 410 | 45 | 2 | 457 | 89.7 | R2 |
| | 449 | 45 | 1 | 495 | 90.7 | R2 |
| | 439 | 31 | 1 | 471 | 93.2 | R2 |
| | 475 | 22 | 1 | 498 | 95.4 | R2 |

FIGS. 3A and 3B and Table 3 show that the construct increased the level of alpha-tocopherol in the transformed plant lines compared with non-transformed plant lines.

Fatty acid compositions are analyzed using gas chromatography from seed of *Arabidopsis* lines transformed with constructs pMON75565 and pMON75571. Table 4 provides a summary of fatty acid levels that are obtained using these constructs. As can be seen, the expression the pMON75565 construct results in increased expression of oleic acid (18:1) and minor decrease in the expression of linoleic acid (18:2) and linolenic acid (18:3), with virtually no change in the levels of stearic acid (18:0). There are no significant changes in 12:0, 14:0, 16:0, 16:1, 20:0, 20:1, 20:2, 22:0, 22:1 and 22:2 fatty acid levels. The results for pMON75571 and pMON75565 differ. Moreover, there is a higher percentage of success using RNAi suppression as compared to sense suppression.

Table 5 provides a summary of oil levels that are obtained using the described constructs. As can be seen, the total levels of protein, carbon, nitrogen and sulfur remain virtually the same when the pMON75565 and pMON75571 constructs are used as compared to the control constructs.

Figure 4:
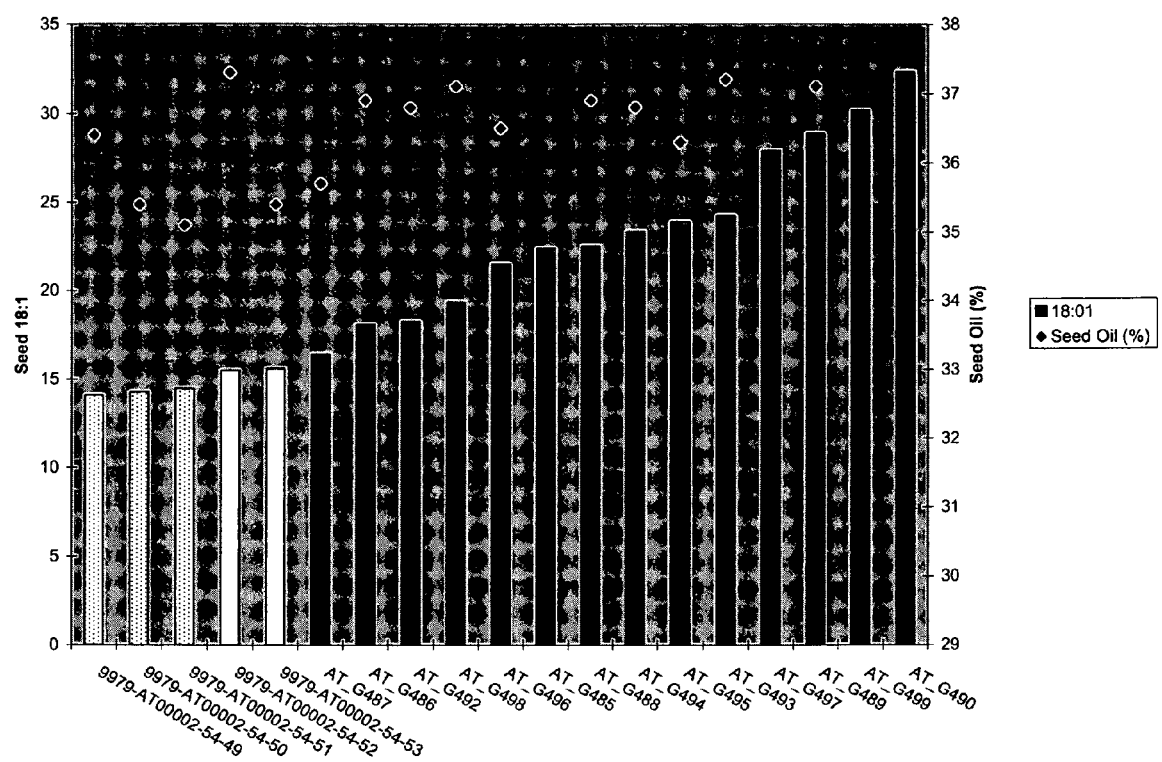
FIG. 4 is a graph representing the average seed oil and oleic fatty acid (18:1) levels in selected *Arabidopsis* seeds from the $R_3$ generation of plants transformed with pMON75565.

FIG. 4 depicts a graphic presentation of both fatty acid and oil levels that are obtained using the pMON75565 and pMON75571 constructs. Lines AT_G490 and AT_G499 (both obtained using pMON75565) have the highest oleic acid and exhibit alpha-tocopherol phenotypes and are both taken onto the next generation for tocopherol and oleic acid and oil analysis. Expression of the double-stranded FAD2 RNA sequences result in the modification of both the fatty acid and the oil compositions.

In order to confirm the phenotype of the pMON75565 construct, the $R_2$ plants expressing the pMON75565 construct are self crossed to obtain $R_3$ plants. Table 6 confirms that the expression of the double-stranded FAD2 RNA sequences by the $R_3$ plants result in the modification of both the fatty acid and the oil compositions. Specifically, the levels of oleic acid are increased as compared to the control construct, and the levels of linoleic and linolenic acid are slightly decreased. Such a result is consistent with a down-regulation of FAD2 expression.

Figure 5A:
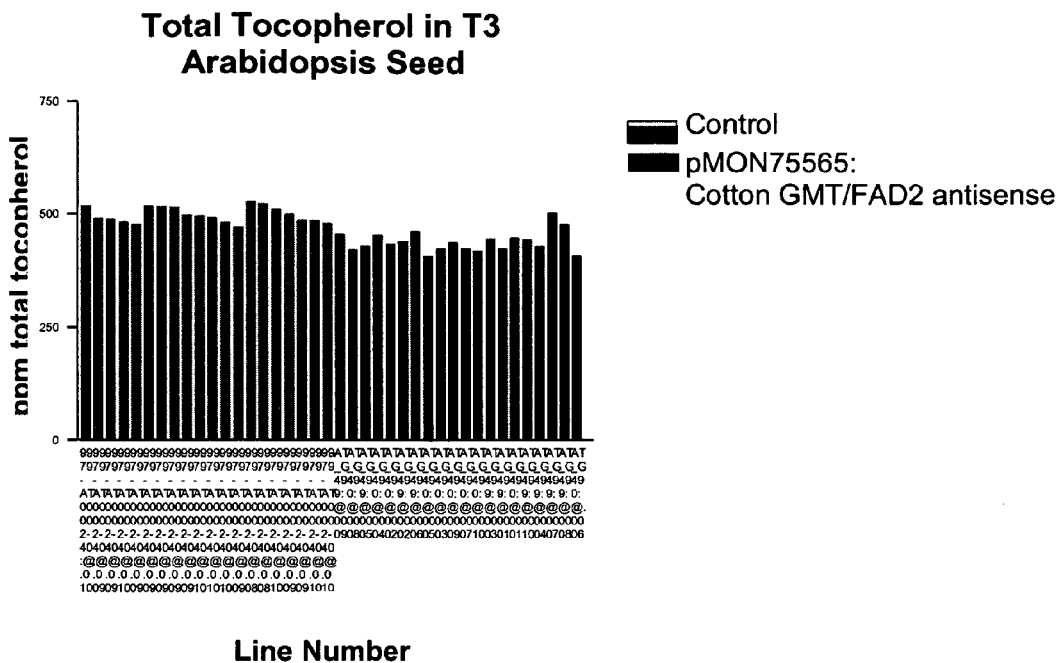
FIGS. 5A and 5B are graphs depicting the total tocopherol levels (FIG. 5A) and percentage of alpha-tocopherol in the total tocopherol content (FIG. 5B) of *Arabidopsis* seeds from the $R_3$ generation of plants transformed with pMON75565.
Figure 5B:
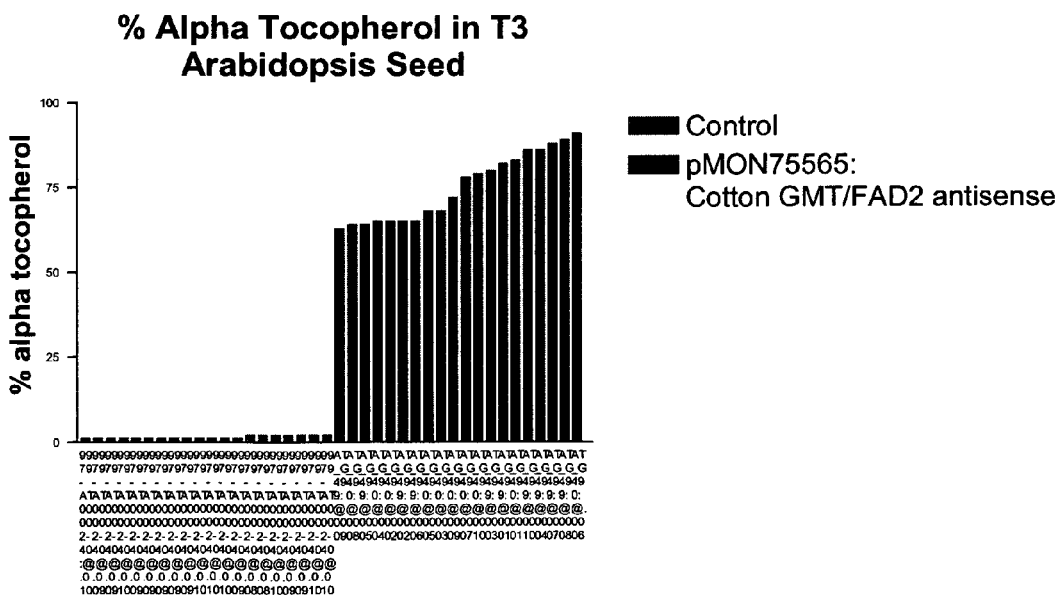

Table 7 and FIG. 5 confirm that the $R_3$ plants express the GMT RNA sequence, which results in increased levels of alpha-tocopherol, while the total levels of tocopherol remain essentially the same.

These data show that the constructs of the present invention up-regulate cotton GMT protein and down-regulate the expression of FAD2. Increased expression of GMT results in an increase in alpha-tocopherol levels. (GMT converts gamma-tocopherol to alpha-tocopherol). An oleic acid level increase and linoleic acid level decrease is consistent with down regulation.

TABLE 4

| CONSTRUCT | STRAIN ID | 18:0 | 18:1 | 18:2 | 18:3 |
|---|---|---|---|---|---|
| Control | 9979-54-49 | 2.98 | 14.09 | 28.71 | 18.88 |
|  | 9979-54-50 | 2.89 | 14.28 | 29.51 | 18.41 |
|  | 9979-54-51 | 2.8 | 14.46 | 29.28 | 18.43 |
|  | 9979-54-52 | 2.75 | 15.5 | 29.53 | 17.57 |
|  | 9979-54-53 | 2.78 | 15.61 | 29.39 | 17.63 |
| pMON 75565 | AT_G485 | 3.04 | 22.4 | 20.82 | 18.38 |
|  | AT_G486 | 2.9 | 18.09 | 25.88 | 18.25 |
|  | AT_G487 | 2.95 | 16.39 | 26.28 | 19.71 |
|  | AT_G488 | 2.97 | 22.53 | 20.95 | 18.16 |
|  | AT_G489 | 2.8 | 28.87 | 18.17 | 15.53 |
|  | AT_G490 | 3 | 32.34 | 15.18 | 15.05 |
|  | AT_G492 | 2.8 | 18.26 | 26.68 | 17.51 |
|  | AT_G493 | 2.86 | 24.25 | 21.16 | 16.85 |
|  | AT_G494 | 3.02 | 23.36 | 20.44 | 18.12 |
|  | AT_G495 | 2.9 | 23.9 | 21.43 | 16.88 |
|  | AT_G496 | 3.02 | 21.53 | 22.08 | 18.59 |
|  | AT_G497 | 2.79 | 27.9 | 17.46 | 16.58 |
|  | AT_G498 | 2.88 | 19.35 | 24.42 | 18.22 |
|  | AT_G499 | 3.04 | 30.19 | 17.08 | 15.55 |
| Control | 9979-54-59 | 2.84 | 14.86 | 29.6 | 17.91 |
|  | 9979-54-60 | 2.83 | 14.96 | 29.41 | 18.14 |
|  | 9979-54-61 | 3.02 | 14.97 | 29.05 | 18.62 |
|  | 9979-54-62 | 2.71 | 14.78 | 29.6 | 18.18 |
|  | 9979-54-63 | 2.95 | 15.29 | 30.13 | 17.43 |
| pMON 75571 | AT_G500 | 2.84 | 15.38 | 28.74 | 18.39 |
|  | AT_G501 | 2.75 | 16.73 | 29.31 | 16.88 |
|  | AT_G502 | 2.85 | 15.86 | 27.86 | 18.79 |
|  | AT_G503 | 2.8 | 17.18 | 29.52 | 16.38 |
|  | AT_G504 | 2.9 | 15.29 | 29.01 | 18.38 |
|  | AT_G505 | 2.93 | 16.25 | 28.94 | 17.59 |
|  | AT_G506 | 2.86 | 16.3 | 29.18 | 17.23 |
|  | AT_G507 | 2.89 | 16.31 | 27.88 | 18.27 |
|  | AT_G508 | 2.98 | 16.44 | 29.93 | 16.73 |
|  | AT_G509 | 2.89 | 15.77 | 28.8 | 17.9 |
|  | AT_G510 | 2.84 | 16.91 | 29.78 | 16.44 |
|  | AT_GS11 | 2.79 | 15.32 | 27.82 | 19.05 |
|  | AT_G512 | 2.77 | 17.88 | 29.68 | 15.62 |
|  | AT_G513 | 2.86 | 16.7 | 29.52 | 16.78 |
|  | AT_G514 | 2.86 | 15.84 | 28.66 | 18.19 |

TABLE 5

| CONSTRUCT | EVENT | GENERATION | % OIL | % PRO | % C | % N | % S | COLOR |
|---|---|---|---|---|---|---|---|---|
| Control | 9979-AT00002-54-49 | R3 | 36.4 | 22.3 | 53.4 | 3.7 | 0.75 | 0.981 |
|  | 9979-AT00002-54-50 | R3 | 35.4 | 22.7 | 52.8 | 3.8 | 0.86 | 0.985 |
|  | 9979-AT00002-54-51 | R3 | 35.1 | 23.5 | 53 | 3.9 | 0.88 | 0.974 |
|  | 9979-AT00002-54-52 | R3 | 37.3 | 21.5 | 53.6 | 3.6 | 0.85 | 0.978 |
|  | 9979-AT00002-54-53 | R3 | 35.4 | 23.5 | 53 | 3.9 | 1.03 | 0.968 |
| pMON 75565 | AT_G485 | R2 | 32 | 25.2 | 51.8 | 4.2 | 0.89 | 0.982 |
|  | AT_G486 | R2 | 36.9 | 22.6 | 53.8 | 3.8 | 0.79 | 0.981 |
|  | AT_G487 | R2 | 35.7 | 23.1 | 53.1 | 3.8 | 0.86 | 0.98 |
|  | AT_G488 | R2 | 36.9 | 22.5 | 53.9 | 3.8 | 0.74 | 0.979 |
|  | AT_G489 | R2 | 37.1 | 22.2 | 53.9 | 3.7 | 0.91 | 0.984 |
|  | AT_G490 | R2 | 37.2 | 22 | 54 | 3.7 | 0.86 | 0.981 |
|  | AT_G492 | R2 | 36.8 | 21.7 | 53.4 | 3.6 | 0.89 | 0.986 |
|  | AT_G493 | R2 | 37.2 | 22.8 | 53.9 | 3.8 | 0.97 | 0.976 |
|  | AT_G494 | R2 | 36.8 | 22.3 | 53.7 | 3.7 | 0.8 | 0.975 |
|  | AT_G495 | R2 | 36.3 | 21.7 | 53.5 | 3.6 | 0.9 | 0.999 |
|  | AT_G496 | R2 | 36.5 | 23 | 53.6 | 3.8 | 0.8 | 0.984 |
|  | AT_G497 | R2 | 35.5 | 23.5 | 53.2 | 3.9 | 0.95 | 0.983 |
|  | AT_G498 | R2 | 37.1 | 22.9 | 53.8 | 3.8 | 0.91 | 0.988 |
|  | AT_G499 | R2 | 36.5 | 22.4 | 53.6 | 3.7 | 0.83 | 0.985 |
| Control | 9979-AT00002-54-59 | R3 | 36.5 | 22.5 | 53.7 | 3.8 | 0.96 | 0.977 |
|  | 9979-AT00002-54-60 | R3 | 36.3 | 22.4 | 53.6 | 3.7 | 0.96 | 0.978 |
|  | 9979-AT00002-54-61 | R3 | 35.9 | 23 | 53.5 | 3.8 | 0.94 | 0.976 |
|  | 9979-AT00002-54-62 | R3 | 36.3 | 22.9 | 53.6 | 3.8 | 1 | 0.977 |
|  | 9979-AT00002-54-63 | R3 | 36 | 22.9 | 53.6 | 3.8 | 0.95 | 0.975 |
| pMON 75571 | AT_G500 | R2 | 37.1 | 22.5 | 53.9 | 3.7 | 0.94 | 0.976 |
|  | AT_G501 | R2 | 36.2 | 22.9 | 53.5 | 3.8 | 1.14 | 0.971 |
|  | AT_G502 | R2 | 36.3 | 23.4 | 53.7 | 3.9 | 1.01 | 0.976 |

TABLE 5-continued

| CONSTRUCT | EVENT | GENERATION | % OIL | % PRO | % C | % N | % S | COLOR |
|---|---|---|---|---|---|---|---|---|
| | AT_G503 | R2 | 36.2 | 22.2 | 53.6 | 3.7 | 1 | 0.98 |
| | AT_G504 | R2 | 37.1 | 22.1 | 53.9 | 3.7 | 0.96 | 0.974 |
| | AT_G505 | R2 | 37.4 | 21.7 | 54 | 3.6 | 0.88 | 0.983 |
| | AT_G506 | R2 | 38 | 21.3 | 54.3 | 3.6 | 0.95 | 0.976 |
| | AT_G507 | R2 | 36.5 | 23.1 | 53.7 | 3.8 | 1.01 | 0.974 |
| | AT_G508 | R2 | 36.9 | 22.2 | 53.8 | 3.7 | 0.97 | 0.981 |
| | AT_G509 | R2 | 36.7 | 22.3 | 53.7 | 3.7 | 0.99 | 0.978 |
| | AT_G510 | R2 | 36.9 | 22.2 | 53.9 | 3.7 | 0.98 | 0.978 |
| | AT_G511 | R2 | 34.8 | 23.8 | 53 | 4 | 1 | 0.982 |
| | AT_G512 | R2 | 35 | 23.7 | 53.2 | 3.9 | 1.15 | 0.973 |
| | AT_G513 | R2 | 36.1 | 22.6 | 53.4 | 3.8 | 0.99 | 0.982 |
| | AT_G514 | R2 | 37.3 | 22.3 | 54 | 3.7 | 0.96 | 0.976 |

TABLE 6

| CONSTRUCT | STRAIN ID | 18:0 | 18:1 | 18:2 | 18:3 |
|---|---|---|---|---|---|
| pMON 75565 | AT_G490-2 | 2.95 | 21.4 | 23.91 | 17.38 |
| | AT_G490-4 | 2.99 | 22.46 | 22.47 | 17 |
| | AT_G490-3 | 2.83 | 22.78 | 22.64 | 17.13 |
| | AT_G490-8 | 2.88 | 22.82 | 22.81 | 16.59 |
| | AT_G490-5 | 3 | 23.33 | 22.51 | 16.51 |
| | AT_G490-6 | 2.93 | 26.1 | 20.29 | 16.02 |
| | AT_G490-7 | 3.07 | 27 | 19.72 | 15.89 |
| | AT_G490-9 | 2.99 | 28.59 | 18.55 | 15.59 |
| | AT_G490-1 | 2.94 | 29.9 | 18.12 | 14.83 |
| | AT_G490-10 | 2.99 | 31.8 | 15.49 | 14.59 |
| | AT_G499-9 | 3.25 | 26.35 | 20.47 | 16.09 |
| | AT_G499-1 | 3.12 | 27.19 | 17.99 | 16.59 |
| | AT_G499-6 | 3.13 | 28.49 | 20.52 | 14.81 |
| | AT_G499-2 | 3.05 | 28.86 | 19.75 | 14.73 |
| | AT_G499-3 | 3.11 | 30.21 | 18.27 | 14.88 |
| | AT_G499-5 | 3.11 | 30.76 | 19.83 | 13.71 |
| | AT_G499-10 | 3.09 | 32.56 | 15.77 | 14.33 |
| | AT_G499-8 | 2.91 | 32.88 | 16.02 | 14.46 |
| | AT_G499-4 | 2.86 | 33.16 | 16.08 | 14.17 |
| | AT_G499-7 | 3.67 | 34.04 | 14.53 | 11.07 |
| Control | 9979-40-92 | 2.74 | 15.3 | 29.07 | 17.16 |
| | 9979-40-94 | 2.64 | 15.9 | 29.02 | 17.16 |
| | 9979-40-95 | 2.81 | 15.92 | 29.03 | 17.35 |
| | 9979-40-88 | 2.85 | 16.17 | 28.87 | 17.14 |
| | 9979-40-97 | 2.79 | 16.42 | 28.9 | 16.58 |
| | 9979-40-90 | 2.56 | 16.5 | 29.15 | 16.45 |
| | 9979-40-93 | 2.72 | 16.65 | 29.22 | 16.31 |
| | 9979-40-91 | 2.67 | 16.84 | 29.61 | 16.33 |
| | 9979-40-96 | 2.78 | 16.88 | 29.07 | 16.44 |
| | 9979-40-89 | 2.71 | 16.92 | 28.88 | 16.51 |
| | 9979-40-100 | 2.67 | 14.86 | 28.84 | 17.59 |
| | 9979-40-105 | 2.81 | 15.08 | 28.3 | 18 |
| | 9979-40-99 | 2.78 | 15.4 | 28.78 | 17.71 |
| | 9979-40-101 | 2.73 | 15.6 | 28.74 | 17.44 |
| | 9979-40-103 | 2.85 | 15.67 | 29.09 | 17.34 |
| | 9979-40-106 | 2.69 | 15.83 | 28.96 | 17.31 |
| | 9979-40-102 | 2.87 | 15.94 | 28.45 | 17.25 |
| | 9979-40-107 | 2.79 | 16.75 | 29.16 | 16.4 |
| | 9979-40-104 | 2.82 | 16.78 | 28.41 | 17.03 |
| | 9979-40-98 | 2.89 | 16.89 | 27.99 | 16.94 |

TABLE 7

| Construct | Strain ID | alpha-Toco | gamma-Toco | delta-Toco | Total Toco | % alpha-Toco | Generation |
|---|---|---|---|---|---|---|---|
| Control | 9979-40-100 | 5 | 495 | 16 | 516 | 1 | R3 |
| | 9979-40-94 | 5 | 469 | 15 | 489 | 1 | R3 |
| | 9979-40-93 | 6 | 468 | 14 | 488 | 1 | R3 |
| | 9979-40-101 | 6 | 461 | 14 | 481 | 1 | R3 |
| | 9979-40-95 | 6 | 455 | 14 | 475 | 1 | R3 |
| | 9979-40-91 | 7 | 491 | 17 | 515 | 1 | R3 |
| | 9979-40-90 | 7 | 491 | 16 | 514 | 1 | R3 |
| | 9979-40-96 | 7 | 490 | 15 | 512 | 1 | R3 |
| | 9979-40-99 | 7 | 473 | 16 | 496 | 1 | R3 |
| | 9979-40-106 | 7 | 471 | 15 | 493 | 1 | R3 |
| | 9979-40-107 | 7 | 469 | 14 | 490 | 1 | R3 |
| | 9979-40-103 | 7 | 458 | 14 | 479 | 1 | R3 |
| | 9979-40-92 | 7 | 447 | 15 | 469 | 1 | R3 |
| | 9979-40-89 | 8 | 498 | 18 | 524 | 2 | R3 |
| | 9979-40-88 | 8 | 496 | 16 | 520 | 2 | R3 |
| | 9979-40-102 | 8 | 485 | 15 | 508 | 2 | R3 |
| | 9979-40-97 | 8 | 474 | 16 | 498 | 2 | R3 |
| | 9979-40-98 | 9 | 462 | 14 | 485 | 2 | R3 |
| | 9979-40-104 | 9 | 460 | 15 | 484 | 2 | R3 |
| | 9979-40-105 | 9 | 453 | 15 | 477 | 2 | R3 |
| pMON75565 | AT_G499-9. | 286 | 161 | 7 | 454 | 63 | R3 |
| | AT_G490-8. | 268 | 143 | 8 | 419 | 64 | R3 |
| | AT_G499-5. | 274 | 147 | 7 | 428 | 64 | R3 |
| | AT_G490-4. | 291 | 153 | 7 | 451 | 65 | R3 |
| | AT_G490-2. | 282 | 143 | 7 | 432 | 65 | R3 |
| | AT_G499-2. | 286 | 145 | 7 | 438 | 65 | R3 |
| | AT_G499-6. | 301 | 152 | 7 | 460 | 65 | R3 |

TABLE 7-continued

| Construct | Strain ID | alpha-Toco | gamma-Toco | delta-Toco | Total Toco | % alpha-Toco | Generation |
|---|---|---|---|---|---|---|---|
| | AT_G490-5. | 274 | 123 | 8 | 405 | 68 | R3 |
| | AT_G490-3. | 285 | 128 | 8 | 421 | 68 | R3 |
| | AT_G490-9. | 312 | 116 | 7 | 435 | 72 | R3 |
| | AT_G490-7. | 330 | 85 | 6 | 421 | 78 | R3 |
| | AT_G490-10. | 330 | 80 | 6 | 416 | 79 | R3 |
| | AT_G499-3. | 352 | 84 | 6 | 442 | 80 | R3 |
| | AT_G499-1. | 344 | 71 | 5 | 420 | 82 | R3 |
| | AT_G490-1. | 368 | 71 | 6 | 445 | 83 | R3 |
| | AT_G499-10. | 380 | 56 | 5 | 441 | 86 | R3 |
| | AT_G499-4. | 368 | 55 | 4 | 427 | 86 | R3 |
| | AT_G499-7. | 441 | 56 | 4 | 501 | 88 | R3 |
| | AT_G499-8. | 423 | 48 | 4 | 475 | 89 | R3 |
| | AT_G490-6. | 367 | 34 | 4 | 405 | 91 | R3 |

All publications and patent applications mentioned in this specification are herein incorporated by reference to the same extent as if each individual publication or patent application was specifically and individually indicated to be incorporated by reference.

What is claimed is:

1. A nucleic acid molecule comprising a first nucleic acid segment encoding a polypeptide, and a second nucleic acid segment for suppression of a polypeptide involved in altering oleic acid content in a plant cell, wherein transcription of said nucleic acid molecule in said cell results in the simultaneous expression of the polypeptide and suppression of fatty acid desaturation in said cell, and wherein said first nucleic acid segment and said second nucleic acid segment are operably linked to a single promoter in a polycistronic configuration.

2. The nucleic acid molecule according to claim 1, wherein said second nucleic acid segment for suppression of a polypeptide involved in altering oleic acid content in a host cell comprises DNA from a FAD2 gene.

3. The nucleic acid molecule according to claim 2, wherein said second nucleic acid segment is expressed as a dsRNA molecule.

4. The nucleic acid molecule according to claim 3, wherein said second nucleic acid segment has at least 21 contiguous nucleotides complementary to the mRNA of the FAD2 gene.

5. The nucleic acid molecule according to claim 4, wherein said second nucleic acid segment has at least 21 contiguous nucleotides from an intron in said FAD2 gene.

6. A plant having in its genome a nucleic acid molecule of claim 1.

7. A soybean plant having in its genome a nucleic acid molecule of claim 1.

* * * * *